US007501271B2

(12) United States Patent
Mizutani et al.

(10) Patent No.: US 7,501,271 B2
(45) Date of Patent: Mar. 10, 2009

(54) PROTEINS HAVING A FLAVONOID 5-O-GLYCOSYLTRANSFERASE ACTIVITY (5GT)

(75) Inventors: Masako Mizutani, Kyoto (JP); Yoshikazu Tanaka, Otsu (JP); Takaaki Kusumi, Suita (JP); Kazuki Saito, Yachimata (JP); Mami Yamazaki, Chiba (JP); Gong Zhizhong, Chiba (JP)

(73) Assignee: International Flower Development Proprietary Limited, Victoria (AU)

( * ) Notice: Subject to any disclaimer, the term of this patent is extended or adjusted under 35 U.S.C. 154(b) by 0 days.

(21) Appl. No.: 11/054,385

(22) Filed: Feb. 10, 2005

(65) Prior Publication Data

US 2005/0257291 A1  Nov. 17, 2005

Related U.S. Application Data

(62) Division of application No. 09/147,955, filed as application No. PCT/JP98/03199 on Jul. 16, 1998, now Pat. No. 6,855,862.

(30) Foreign Application Priority Data

Jul. 25, 1997  (JP) .................................. 9-200571

(51) Int. Cl.
*C12N 9/10* (2006.01)
*C07H 21/02* (2006.01)
*C07H 15/24* (2006.01)
*C12P 21/06* (2006.01)
*C12P 21/04* (2006.01)

(52) U.S. Cl. ........................ 435/193; 536/23.6; 536/6.3; 435/69.1; 435/70.1

(58) Field of Classification Search ........................ None
See application file for complete search history.

(56) References Cited

U.S. PATENT DOCUMENTS

| 5,859,334 A | 1/1999 | Brugliera et al. |
| 5,919,998 A | 7/1999 | Bandurski et al. |

FOREIGN PATENT DOCUMENTS

| EP | 0 771 878 A1 | 5/1997 |
| JP | 7-509139 | 10/1995 |
| WO | WO 94/03591 | 2/1994 |
| WO | 96/00291 | 1/1996 |
| WO | 97/16559 | 5/1997 |

OTHER PUBLICATIONS

Kamsteeg et al. (1978) Biochemical Genetics, vol. 16, p. 1059-1071.*
Teusch et al. (1986) Planta, vol. 168, p. 586-591.*
Vogt et al. (1997) Planta, vol. 203, p. 349-361.*
Vogt et al (1999) The Plant Journal, vol. 19, p. 509-519.*
Vogt, T. (2002) Planta, vol. 214, p. 492-495.*
Taguchi et al. (2003) Archives of biochemistry and biophysics, vol. 420, p. 95-102.*
Jonssen et al. (1984) Planta, vol. 160, p. 341-347.*
Ausubel et al. (1993) "Current Protocols in Molecular Biology" Unit 2.10, John Wiley and Sons, Inc., New York, pp. 1-16.*
Dufresne, Guilaume, et al., Genetice Sequences: How Are They Patented?, Nature Biotechnology, vol. 22, No. 2, Feb. 2004, 232-232.
Lawrence, Eleanor, Henderson's Dictionary of Biological Terms, Tenth Edition, Longman Scientific & Technical, 1990, p. 237.
Szerszen et al., "*iaglu*, a Gene from *Zea* mays Involved in Conjugation of Growth Hormone Indole-3-Acetic Acid," *Science*, 1994, vol. 265, pp. 1699-1701, American Association for the Advancement of Science, Washington, D.C.
Sambrook et al., "Expression of Cloned Genes in Cultured Mammalian Cells," *Molecular Cloning—A Laboratory Manual*, 1989, Second Edition, pp. 16.2-17.27, Cold Spring Harbor Laboratory Press, Woodbury, New York.
Kossman et al., "Transgenic plants as a tool to understand starch biosynthesis," *Progress in Biotechnology*, 1995, vol. 10, pp. 272-278, Proc. Int. Conf. Apr. 23-26, Elsevier Science B.V., London, England.
Broun et al., "Catalytic Plasticity of Fatty Acid Modification Enzymes Underlying Chemical Diversity of Plant Lipids," *Science*, 1998, vol. 282, pp. 1315-1317, American Association for the Advancement of Science, Washington, D.C.
Lazar et al., "Transforming Growth Factor α: Mutation of Aspartic Acid 47 and Leucine 48 Results in Different Biological Activities," *Molecular and Cellular Biology*, 1988, vol. 8, No. 3, pp. 1247-1252, American Society for Microbiology, Washington, D.C.
Bandurski et al., Sequence Search Results, Genbank Accession No. Q41819, Aug. 1, 2000.
Kojima et al., "*Nicotiana tabacum* mRNA for glucosyl transferase," complete cds, Database Accession No. AB000623, Jan. 2, 1997 (XP-002276244—Abstract).
Graham et al., "*Arabidopsis thaliana* UDP-glucose: indole-3-acetate beta-D-glucosyltransferase (iaglu) mRNA," complete cds, *Biochemistry and Biophysics*, 1997, Iowa State University, Ames, Iowa, Database Accession No. U81293 (XP-002276245—Abstract).
Kamsteeg et al., "Identification, Properties, and Genetic Control of UDP-Glucose: Cyanidin-3-Ryamnosyl-(1-6)-Glucoside-5-O-Glucosyltransferase Isolated from Petals of the Red Campion (*Silene dioica*)," *Biochemical Genetics*, 1978, vol. 16, Nos. 11/12, Plenum Publishing Corporation, The Netherlands.

(Continued)

*Primary Examiner*—Richard Hutson
*Assistant Examiner*—Alexander D Kim
(74) *Attorney, Agent, or Firm*—Drinker Biddle & Reath LLP

(57) ABSTRACT

The present invention provides a gene that codes for a protein, wherein the protein is an anthocyanin 5-O-glucosyltransferase, which is an enzyme that transfers a glycoside to the 5 position of a flavonoid. The disclosed anthocyanin 5-O-glucosyltransferases were isolated from *Perilla fruescens*, *Verbena hybrida*, *Torenia hybrida*, and *Petunia hybrida*. Also disclosed are genes that code for a protein having a modified amino acid sequence relative to the above amino acid sequence and having activity that transfers a glycoside to the 5 position of a flavonoid, and a process for producing the above protein using said gene. This gene can be used to artificially alter the color of plants.

5 Claims, No Drawings

OTHER PUBLICATIONS

Schwinn et al., "Expression of an *Antirrhinum majus* UDP-glucose:flavonoid-3-O-glucosyltransferase transgene alters flavonoid glycosylation and acylation in lisianthus (*Eustoma grandiflorum* Grise.)" *Plant Science*, 1997, vol. 125, pp. 53-61, Elsevier Science, Ireland, Ltd., Ireland.

Martin et al., "Control of anthocyanin biosynthesis in flowers of *Antirrhinum majus*," *The Plant Journal*, 1991, vol. 1, No. 1, pp. 37-49, Blackwell Science, Oxford, England.

Teusch et al., "Genetic control of UDP-glucose: anthocyanin 5-O-glucosyltransferase from flowers of *Matthiola incana* R.Br.," *Planta Medica*, 1986, vol. 168, pp. 586-591, Georg Thieme Verlag, Stuttgart, Germany.

Harborne et al., *The Handbook of Natural Flavonoids*, 1999, vol. 2, Wiley & Sons, Ltd., New York.

Heller, "Flavonoid Biosynthesis, An Overview," Plant Flavonoids in Biology and Medicine: Biochemical, Pharmacological, and Structure-Activity Relationships, Proceedings of a Symposium Held in Buffalo, New York, Jul. 22-26, 1985, pp. 25-42, Alan R. Liss, New York.

Heller et al. "Biosynthesis of Flavonids," *The Flavonids: Advances in Research Since 1986*, edited by J.B. Harborne, 1993, Chapman & Hall, London, England.

Office Action issued Jun. 17, 2008, by Japanese Patent Office in Japanese Application No. 11-509647.

* cited by examiner

PROTEINS HAVING A FLAVONOID 5-O-GLYCOSYLTRANSFERASE ACTIVITY (5GT)

TECHNICAL FIELD

The present invention relates to a gene coding for a protein having activity that transfers a glycoside to the 5 position of a flavonoid, and a process utilizing that gene.

BACKGROUND ART

The flower industry strives to develop various new varieties. Changing the color of a flower is one way of effectively breeding a new variety. A wide range of colors have been successfully produced for nearly all commercial varieties using classical breeding methods. With these methods, however, since there are restrictions on the gene pool for each species, it is rare for a single species to have a broad range of colored varieties.

Flower colors are based on two types of pigments, namely flavonoids and carotinoids. Flavonoids contribute to color tones ranging from yellow to red and blue, while carotinoids contribute to color tones of orange or yellow. Flavonoid molecules that primarily contribute to flower color are anthocyanins which are glycosides of cyanidin, delphinidin, petunidin, peonidin, malvidin and pelargonidin, and different anthocyans cause remarkable changes in flower color. Moreover, flower color is also affected by auxiliary coloring by colorless flavonoids, metal complex formation, glucosylation, acylation, methylation and vacuolar pH (Forkmann, Plant Breeding, 106, 1, 1991).

The biosynthesis route of anthocyanins, which begins with phenylalanine, has been well understood (e.g., Plant Cell, 7, 1071-1083, 1995), and nearly all genes involved in the biosynthesis have been cloned. For example, among those genes thought to be involved in biosynthesis of malonylshisonin (3-0-(6-0-(p-cumaloyl)-β-D-glucosyl)-5-0-(6-0-malonyl-β-D-glucosyl)-cyanidin), which is an anthocyanin of *Perilla*, those genes for which homologues have not yet been reported are only the flavonoid-3'-hydroxylase, UDP-glucose: anthocyanin (flavonoid) 5-0-glucosyl transferase (abbreviated as 5GT) and malonyl group transferase genes.

Among these, flavonoid-3'-hydroxylase is known to belong to the cytochrome P450 gene family (Plant Cell, 7, 1071-1083, 1995), and cytochrome P450 genes are surmised to demonstrate structural homology.

The hydroxyl group at the 3 position of flavonoid molecules is typically modified by glucose, and generally glucosylation and other modifications by glycoside are considered to increase the stability and solubility of anthocyanins (The Flavonoids, Chapman & Hall, 1994).

Genes coding for the UDP-glucose: anthocyanidin or flavonoid-3-glucosyl transferase (abbreviated as 3GT) that catalyze this reaction are obtained from numerous plants such as corn, barley, snapdragons and gentians, and their amino acid sequences mutually demonstrate significant homology. For example, the homology between the 3GT amino acid sequences of monocotyledonous corn and dicotyledoneous gentian is 32%, that between the 3GT amino acid sequences of monocotyledonous corn and monocotyledonous barley is 73%, and that between the 3GT amino acid sequences of dicotyledonous gentian and dicotyledonous eggplant is 46%.

In addition, the gene coding for UDP-ramnose: anthocyanidin 3-glucosidoramnosyl transferase (3RT) of petunias has also been cloned.

However, even though the hydroxyl group at the 5 position of the flavonoids of numerous plants is glucosylated, a gene for the enzyme (5GT) that catalyzes this reaction has yet to be obtained.

In addition, although there are examples of measuring the reaction by which glycoside is transferred to the 5 position of *petunia* and stock anthocyanins (Planta, 160, 341-347, 1984, Planta, 168, 586-591, 1986), these reports only describe the investigation of enzymological properties using crude extracts or partially purified products of flower petals, and there are no examples of this enzyme being purified to its pure form. In addition, since glycosyltransferases are typically biochemically unstable, enzyme purification is difficult.

Although there are hardly any cases in which color tone is changed by addition of glycoside to a flavonoid molecule, since aromatic acyl groups that have a significant effect on color tone are linked to a glucose molecule or ramnose molecule within an anthocyanin, regulation of the glycoside transfer reaction is important in terms of controlling anthocyanin biosynthesis, and ultimately in controlling flower color. Furthermore, as an example of changing flower color by regulating the expression of glycosyltransferase gene, the reaction by *petunia* 3RT has been controlled in transformed *petunia* to modify flower color.

Plant species, which can be transformed with a foreign gene, include, for example, roses, chrysanthemums, carnations, daisies, petunias, torenia, bellflowers, calanchoes, tulips and gladiolas.

DISCLOSURE OF THE INVENTION

The inventors of the present invention therefore sought to obtain a gene that codes for a protein having activity that transfers a glycoside to the 5 position of a flavonoid, thereby leading to completion of the present invention.

For example, the 5 position hydroxyl group of the anthocyanins of chrysanthemums and some of the anthocyanins of roses and carnations are not glucosylated. The anthocyanin structure can be changed by introducing the 5GT gene obtained by the present invention into these plants.

In addition, although it is possible to change flower color and stabilize flavonoids by acylating flavonoids using the acyl group transferase gene described in International Publication No. WO96/25500, since the acyl group does not bond directly with the flavonoid, but rather bonds by way of a sugar, simply introducing an acyl group transferase gene alone is not sufficient for changing flower color and may even cause the flavonoid not to become stable.

However, by introducing the 5GT gene in combination with an acyl group transferase gene, sugar is bounded to the 5 position of the flavonoid thereby further allowing the flavonoid to be acylated. This can be expected to change the anthocyanin structure and cause the flower color to become bluish.

In addition, if expression of 5GT gene of a plant in which the 5 position of anthocyanin is glucosylated is suppressed with the antisense method or co-suppression method and so forth, transfer of glucose residue to 5 position can be inhibited. So that, flower color can be changed. For example, suppressing 5GT activity in gentian or bellflower can be expected to cause flower color to become reddish.

The inventors of the present invention isolated cDNA of 5GT from *Perilla, torenia, verbena* and *petunia* plants using gene recombination technology, and determined the nucleotide sequence of the structural gene. Namely, the inventors of the present invention provide a DNA sequence that codes for 5GT present in the tissue that expresses anthocyanins in these plants. Moreover, since this enzyme transfers glycoside to the 5 position of anthocyanin pigment, it can be used to change flower color and increase anthocyanin stability.

EMBODIMENT FOR CARRYING OUT THE INVENTION

The method of differential displacement, for example, can be used to obtain DNA that codes for the enzyme of the present invention. In *Perilla* (*Perilla frutescens*), for example, there are varieties that accumulate anthocyanins (e.g., red forma) and those that do not (e.g., green forma). By cloning DNA present in varieties that accumulate anthocyanins but not present in varieties that do not, it is possible to obtain the DNA that codes for the enzyme of the present invention.

More specifically, RNA is extracted from the leaves of red forma and green forma, and cDNA is synthesized in accordance with standard methods. This is then separated by electrophoresis to isolate cDNA present in the cDNA library of red forma but not present in the cDNA library of green forma. Next, the red forma cDNA library is screened using the resulting cDNA as a probe to obtain the cDNA that codes for the enzyme of the present invention.

Once cDNA that codes for the enzyme of the present invention is obtained in the manner described above, this cDNA or its fragment is used as a probe to screening the cDNA libraries of other plants. As a result, the DNA that codes for the enzyme of the present invention can be obtained from those plants.

As an example of the screening, in the present invention, the DNA coding for the enzyme of the present invention is cloned from *Perilla* by the differential display method (Example 1). Next, DNA that codes for the enzyme of the present invention is obtained from *verbena* by screening of cDNAs from *verbena* (*Verbena hebrida*) using the cloned DNA of Example 1 as a probe (Example 2). Moreover, DNA coding for the enzyme of the present invention is obtained from *torenia* in the same manner (Example 3).

Then, it was confirmed that the proteins encoded in these DNAs have the enzymatic activity of the present invention.

Moreover, the DNA coding for the enzyme of the present invention was obtained from *petunia* (Example 4).

Examples of the DNAs of the present invention include that which codes for the amino acid sequence described in any one of SEQ ID NOs: 2, 4, 6, 8, or 12. However, proteins having an amino acid sequence modified by addition and/or deletion of one or more amino acids and/or substitutions by one or more other amino acids are also known to maintain enzymatic activity similar to the original protein. Thus, genes coding for a protein that has an amino acid sequence modified by addition and/or deletions of one or more amino acids and/or substitutions by one or more other amino acids relative to the amino acid sequence described in any one of SEQ ID NOs: 2, 4, 6, 8, or 12, and still maintains activity of transferring a glycoside to the 5 position of a flavonoid, also belong to the present invention.

The present invention also relates to a gene coding for a protein which gene hybridizes to a nucleotide sequence described in any one of SEQ ID NOs: 1, 3, 5, 7, or 11, or to a nucleotide sequence that codes for an amino acid sequence described therein or to their portions, for example a portion coding for at least six amino acids of a consensus region, under conditions of 2 to 5×SSC, and for example, 5×SSC, and 50° C., and that has activity of transferring a glycoside to the 5 position of a flavonoid. Furthermore, the optimum hybridization temperature varies according to the nucleotide sequence and its length, and it is preferable that the hybridization temperature be lower the shorter the nucleotide sequence. For example, a temperature of 50° C. or lower is preferable in the case of a nucleotide sequence (18 bases) coding for six amino acids.

Although examples of genes selected by hybridization in this manner include those which are naturally-occurring such as those derived from plants, examples of which include a gene derived from *verbena* and *torenia*, they may also be those derived from other plants, examples of which include petunias, roses, carnations and hyacinths. In addition, genes selected by hybridization may also be cDNA or genomic DNA.

Moreover, the present invention also relates to a gene coding for a protein having an amino acid sequence having homology of 30% or more, preferably 50% or more, for example 60% or 70% or more, and in some cases, 90% or more relative to an amino acid sequence of any of SEQ ID NOs: 2, 4, 6, 8, or 12, and having activity that transfers a glycoside to the 5 position of a flavonoid. Namely, as indicated in Examples, DNA coding for the enzyme of the present invention demonstrates homology of 20 to 30% in comparison with other glycosyltransferase genes. Thus, the present invention includes genes coding for a protein that having homology of 30% or more with an amino acid sequence described in any one of SEQ ID NOs: 2, 4, 6, 8, or 12, and has glycosyltransferase activity.

In addition, as is clear from a comparison of the results of Examples 1 through 4, the amino acid sequence of the enzyme of the present invention varies according to the species, with interspecies homology being 50% or more (see Examples 3 and 4), and for example 60 to 70% (see Example 2), while the homology of the amino acid sequences of the enzymes derived from the same species is 90% or more (see Example 1). Thus, genes coding for a protein that has an amino acid sequence having homology of 50% or more, for example 60-70% or more, and in some cases, 90% or more, relative to an amino acid sequence described in any one of SEQ ID NOs: 2, 4, 6, 8, or 12, and maintains the glycosyltransferase activity of the present invention are included in the present invention.

As is described in detail in Examples, DNA having a native nucleotide sequence is obtained by, for example, screening of a cDNA library.

In addition, DNA coding for an enzyme having a modified amino acid sequence can be synthesized using ordinary site-specific mutagenesis and PCR based on the nucleotide sequence of a native DNA. For example, a DNA fragment containing a site at which a modification is desired to be introduced is obtained by restriction enzyme digestion of cDNA or genomic DNA obtained as described above. By using this as a template, site-specific mutagenesis or PCR is performed using a primer containing the desired mutation to obtain a DNA fragment containing the desired modification. This is then ligated to DNA coding for another portion of the target enzyme.

Alternatively, in order to obtain DNA coding for an enzyme having a shortened amino acid sequence, for example, DNA coding for an amino acid sequence that is longer than the target amino acid sequence, for example that coding for the entire amino acid sequence, is digested by a desired restriction enzyme, and in the case the resulting DNA fragment does not code for the entire target amino acid sequence, the deficient portion should be supplemented by ligating synthetic DNA.

In addition, by expressing this clone using a gene expression system in *E. coli* or yeast and measuring enzyme activity, the resulting gene can be confirmed to code for glycosyltransferase, and by clarifying the translation region of glycosyltransferase gene that transfers glycoside to the 5 position of a flavonoid, a gene is obtained that codes for the glycosyltransferase claimed in the present invention. Moreover, by expressing said gene, the target transferase protein that transfers a glycoside to the 5 position of a flavonoid can be obtained.

Alternatively, the protein can be obtained by using antibody to an amino acid sequence described in any one of SEQ ID NOs: 2, 4, 6, 8, or 12.

Thus, the present invention also relates to a recombinant vector containing the above-mentioned DNA, and more particularly, to an expression vector and a host transformed with the vector. Both prokaryotes and eukaryotes can be used for the host. Examples of prokaryotes that can be routinely used for the host include bacteria, for example, the genus *Escherichia* such as *Escherichia coli*, and the genus *Bacillus* such as *Bacillus subtilis*.

Examples of eukaryotes that can be used include lower eukaryotes such as eucaryotic microorganisms including fungi such as yeast or mold. Examples of yeast includes the genus *Saccharomyces* such as *Saccharomyces cerevisiae*, while examples of molds include the genus *Aspergillus* such as *Aspergillus oryzae* and *Aspergillus niger*, as well as the genus *Penicillium*. Moreover, animal or plant cells can also be used, examples of animal cells including mouse, hamster, monkey and human cell systems. Moreover, insect cells such as silkworm cells or adult silkworms themselves can be used as hosts.

The expression vectors of the present invention contain an expression control region, such as a promoter, terminator or an origin of replication, depending on the type of host in which they are to be introduced. Examples of promoters of bacterial expression vectors include conventionally used promoters such as trc promoter, tac promoter and lac promoter, while examples of yeast promoters include glyceroaldehyde triphosphate dehydrogenase promoter and PH05 promoter. Examples of mold promoters include amylase and trpC. In addition, examples of promoters for animal cell hosts include viral promoters such as SV40 early promoter and SV40 late promoter.

Preparation of expression vector can be performed in accordance with standard methods using restriction enzyme, ligase and so forth. In addition, transformation of a host by an expression vector can also be performed in accordance with standard methods.

In the process for producing the above-mentioned protein, a host transformed with the expression vector is cultured, cultivated or bred, the target protein can be recovered and purified from the resulting culture in accordance with standard methods, examples of which include filtration, centrifugation, cell homogenation, gel filtration chromatography and ion exchange chromatography.

Furthermore, although the present specification describes transferases derived from *Perilla, verbena, torenia* and *petunia* wherein the transferases that transfer glycoside to the 5 position of a flavonoid (which may be simply referred to as "glycosyltransferase" in the present invention), a gene that codes for said enzyme can be cloned, by entirely or partially altering the purification method of said enzyme so as to purify a glycosyltransferase of another plant, and determining the amino acid sequence of said enzyme. Moreover, by using cDNA of the glycosyltransferase derived from *Perilla* of the present invention as a probe, cDNA of a different glycosyltransferase was able to be obtained from *Perilla*, and cDNA of a different glycosyltransferase was able to be obtained from a different plant. Thus, other glycosyltransferase genes can be obtained by using a portion or the entirety of a glycosyltransferase gene.

In addition, as indicated in the present specification, by purifying glycosyltransferase from *Perilla, verbena, torenia* and *petunia* to obtain antibody to said enzyme in accordance with standard methods, cDNA or chromosomal DNA produces protein which reacts with that antibody that can be cloned. Thus, the present invention is not limited to only genes of glycosyltransferases derived from *Perilla, verbena, torenia* and *petunia*, but also relates to glycosyltransferase in the broad sense.

Moreover, the present invention also relates to a plant, its progeny or their tissue for which color has been adjusted by introduction of glycosyltransferase gene, and their form may be that of cut flowers as well.

In addition, UDP-glucose is an example of a glycoside donor in the glycoside transfer reaction of glycoside that include anthocyanin in the present specification.

EXAMPLES

The following provides a detailed explanation of the present invention based on Examples. Unless specified otherwise, the experimental procedure was performed in accordance with the methods described in Molecular Cloning (Cold Spring Harbor, 1989), New Biochemistry Experimental Manual (Kagaku Dojin, 1996) and International Patent Laid-Open Publication No. WO96/25500.

Example 1

Cloning of a Gene Specifically Expressed in Red Forma (1) Differential Display

*Perilla* (*Perilla frutescens*) includes varieties that accumulate anthocyanins in their leaves (for example, red forma (Sakata-no-tane)), and varieties that do not accumulate anthocyanins (for example, blue forma (Sakata-no-tane)). The structure of the major anthocyanin is reported to be malonylshisonin (3-0-(6-0-(p-cumaloyl)-β-D-glucosyl)-5-0-(6-0-malonyl-β-D-glucosyl)-cyanidin) (Agri. Biol. Chem., 53:197-198, 1989).

Differential display is a method reported in Science, 257, 967-971 (1992), and is used, for example, to obtain genes that are expressed tissue-specifically.

Total RNA was extracted from the leaves of the above-mentioned two types of *Perilla* by the hot phenol method (Plant Molecular Biology Manual, Kluwer Academic Publishers, 1994, pp. D5/1-13). Poly A+RNA was purified from the resulting total RNA using an mRNA separator kit (Clonetech). 0.9 µg of poly A+RNA were reverse-transcribed in 33 µl of reaction mixture using oligo-dT primer added an anchor (GenHunter, H-T11G, H-TL11A and H-T11C) to obtain single strand cDNA. Using this cDNA as a template, PCR was performed using the same oligo-dT primer added an anchor and synthetic primers (GenHunter, H-AP1 through 8) as primers.

The volume of the PCR reaction mixture was 20 µl, and it contained 2 µl of cDNA solution, 0.2 µM of any one of H-T11G, H-T11A or H-T11C primer, 0.2 µM of any primer from H-AP1 through H-AP8, 0.12 µM dNTP, 5 or 10 µCi of [$^{32}$P]dCTP, 10 mM Tris-HCl (pH 9.0), 50 mM KCl, 0.01% Triton X-100, 1.25 mM MgCl$_2$ and 1 unit of Taq polymerase. The reaction conditions comprised holding the temperature at 72° C. for 20 seconds followed by repeating the reaction for 40 cycles with one cycle comprising raising the temperature to 94° C. for 30 seconds, lowering to 40° C. for 2 minutes and raising to 72° C. for 30 seconds, and then holding the temperature at 72° C. for 5 minutes.

The DNA fragments amplified in this manner were separated by the same polyacrylamide gel electrophoresis as used for DNA Sequencing. After drying the gel, the gel was exposed to X-ray film. Among the resulting approximately 2,600 bands, there were 36 bands observed only in the red forma as a result of comparing the two varieties. They were cut out of the dried gel and eluted into 100 μl of water. The eluted DNA was precipitated with ethanol and dissolved in 20 μl of water. Using a half amount of each DNA as a template, the PCR reaction was performed as described above, and amplified fragments were obtained for 33 of DNA fragments. Library screening and northern analysis were then performed using these DNA fragments.

(2) Northern Analysis

Northern analysis was performed according to the method described below using the above 33 types of DNA probes. After separating poly A+RNA derived from red forma and green forma with formamide gel containing 1.2% agarose, the poly A+RNA was transferred to a Nylon membrane. This membrane was hybridized with the above-mentioned DNA probes labeled with [$^{32}$P] for overnight at 65° C. in the presence of 5XSSPE, 5X Denhalt's solution, 0.5% SDS and 20 μg/ml of denatured salmon sperm DNA. The hybridized membrane was washed at 65° C. in 1XSSPE and 0.1% SDS solution and subjected to autoradiography. As a result, only five probes were specifically expressed in red forma. These clones are predicted to be genes involved in the biosynthesis of anthocyanins.

(3) Screening of cDNA Library

A cDNA library with λgt10 as a vector was prepared using the poly A+RNA obtained from the leaves of red forma and the Complete Rapid Cloning System λgt10 (Amersham). This cDNA library was screened with the five DNA fragments described above to obtain cDNA corresponding to each fragment. Among these, a clone named 3R5 was obtained using a DNA fragment obtained by H-T11A and H-AP3 primers, and this clone demonstrated homology of approximately 26% at the amino acid level with previously reported corn flavonoid-3-0-glucosyl transferase.

In addition, clones designated as 3R4 and 3R6 were obtained by library screening using the same probes, and these demonstrated an extremely high level of homology with 3R5. The complete nucleotide sequences and deduced amino acid sequences of 3R4 and 3R6 are shown in SEQ ID NO: 1 and SEQ ID NO: 3 of the Sequence Listing, respectively. In addition, the deduced amino acid sequences of the proteins encoded by 3R4 and 3R6 demonstrated homology of 92%.

A clone designated as 8R6 was obtained using a DNA fragment obtained by H-T11G and H-AP8 primers, and this clone did not demonstrate significant homology with any sequences reported so far. This sequence is shown in SEQ ID NO: 5 of the Sequence Listing. Although there is a strong possibility that 8R6 is a gene involved in the biosynthesis of anthocyanins, since its structure lacks homology with genes reported so far, it is predicted to be a new gene involved in anthocyanin biosynthesis.

In consideration of the anthocyanin structure in *Perilla* (the previously mentioned malonylshisonin), it is predicted that this gene is a malonyl transferase. In order to verify this, this gene should be expressed in yeast and *E. coli* followed by reacting with anthocyanin and malonyl-CoA as substrates. Such an experiment can be carried out using, for example, the method described in International Publication No. WO96/ 25500. Malonyl transferase gene is useful in terms of artificially altering anthocyanin structure.

(4) Expression of 3R4 cDNA in Yeast

An approximately 1.5 kb DNA fragment obtained by blunting the BstXI cleavaged site of p3R4 using T4 DNA polymerase (Takara Shuzo) and then cutting out at the BamHI cleavage site in the adapter, and an approximately 8 kb DNA fragment obtained by blunting the EcoRI cleaved end of pYE22m and then digesting with BamHI were ligated to obtain a plasmid that was designated as pY3R4.

Furthermore, *E. coli* strain JM109 having pYE22m was named *Escherichia coli* SBM335, and deposited at the National Institute of Bioscience and Human-Technology Agency of Industrial Science and Technology as FERM BP-5435. In pY3R4, cDNA coding for glycosyltransferase has been ligated downstream of the promoter for glyceroal-dehyde triphosphate dehydrogenase lone of the constitutive yeast promoter, and transcription is controlled by this promoter.

Using pY3R4, yeast *Saccharomyces cerevisiae* G1315 (Ashikari, et al., Appl. Microbiol. Biotechnol., 30, 515-520, 1989) was transformed according to the method of Ito, et al. (Ito, et al., J. Bacteriol., 153, 163-168, 1983). The transformed yeast was selected according to recovery of tryptophan synthesis ability. The resulting transformed strain was cultured for 24 hours at 30° C. with shaking in 10 ml of Burkholder's medium (Burkholder, Amer. J. Bot., 30, 206-210) containing 1% casamino acids.

In order to conduct a control experiment, yeast that spontaneously recovered tryptophan synthesis ability was also cultured in the same manner. After collecting the yeast, the cells were suspended in suspension buffer (100 mM phosphate buffer (pH 8.5), 0.1% (v/v) 2-mercaptoethanol, 10 μM APMSF and 100 μM UDP-glucose) followed by the addition of glass beads (Glass Beads, 425-600 microns Acid-Wash, Sigma) and vigorous shaking to crush the cells. The crushed cells were then centrifuged for 20 minutes at 15,000 rpm and the supernatant was used as a crude enzyme solution for the measurement of enzyme activity described below.

(5) Measurement of Enzymatic Activity

After allowing 50 μl of reaction mixture containing 20 μl of crude enzyme solution (100 mM phosphate buffer (pH 8.5), 670 μM cyanidin-3-glucoside, 1 mM UDP-glucose) for 10 minutes at 30° C., 50 μl of 50% acetonitrile solution containing 0.1% TFA was added to stop the reaction. Supernatant obtained by centrifuging for 5 minutes at 15,000 rpm was passed through a Samprep LCR4(T)-LC filter (Millipore) so as to remove impurities. This was then analyzed by high-performance liquid chromatography (HPLC). Analysis was performed using a reverse phase column (Asahipak ODP-50, 4.6 mm diameter×250 mm, Showa Denko), the mobile phase consisted of 0.5% TFA/H$_2$O for solution A and 0.5% TFA 50% CH$_3$CN for solution B. The flow rate was 0.6 ml/min. and the fractions were eluted at a gradient of B20%→B100% (20 min) followed by holding at B100% for 5 minutes.

20 μl of reaction mixture was used for analysis. A520 nm, AUFS 0.5 (Shimadzu SPD-10A) and a photodiode array detector (Shimadzu SPD-M6A) at an absorbance of 600-250 nm were used for detection. In the case of reaction of yeast crude enzyme solution that expressed pY3R4, in addition to the substrate cyanidin-3-glucoside (retention time: 17 minutes), a new peak was observed at retention time of 14.5 minutes. Since it was not observed in the case of reaction of yeast crude enzyme solution of the control experiment, this new peak was considered to be generated due to the activity of protein originated from pY3R4. As a result of co-chromatography with cyanidin-3,5-diglucoside, the retention time of this peak coincided with that of cyanidin-3,5-diglucoside, and their absorption spectra were also identical to each other. Based on these observations, 3R4 cDNA of *Perilla* was found to code for 5GT.

Example 2

Cloning of 5GT Gene of *Verbena hybrida*

(1) Preparation of cDNA Library

Petals were collected from *Verbena* variety *Hanatemari violet* (Suntory) and ground by a mortar and pestle in liquid nitrogen. RNA was extracted from the ground tissues according to a method using guanidine thiocyanate/cesium chloride, and poly A+RNA was obtained by the method recommended by the manufacturer using Oligotex (Takara Shuzo). The method using guanidine thiocyanate/cesium chloride was carried out in accordance with the method described in detail in Methods in Molecular Biology, Vol. 2 (Humana Press Inc., 1984) by R. McGookin and Robert J. Slater, et al.

Using the resulting poly A+RNA as a template, double-stranded cDNA was synthesized using the ZAP-cDNA synthesis kit (Stratagene), then, a cDNA library was prepared using the Uni-ZAP XR Cloning Kit (Stratagene) according to the method recommended by the manufacturer.

(2) Cloning of 5GT cDNA

The λ phage library obtained as described above was screened in the following manner using the p3R4 cDNA of *Perilla* as a probe. The filters were maintained at 42° C. for 1 hour in hybridization buffer (5XSSC, 30% formamide, 50 mM sodium phosphate buffer (pH 7.0), 3% SDS 2% blocking reagent (Boehringer), 0.1% lauroylsarcosine, 80 μg/ml of salmon sperm DNA). DIG-labeled *Perilla* 5GT cDNA, p3R4 cDNA, fragment was added to the hybridization solution and the filters were incubated for further 16 hours.

After washing the filters with washing solution (5X SSC 50° C., 1% SDS), the positive clones labeled with anti-DIG-alkaline phosphate were immunologically detected using 5-bromo-4-chloro-3-indolylphosphate and nitro blue tetrazolium salt according to the method described by the manufacturer (Boehringer).

As a result, seven positive clones were obtained. These cDNA were excised on plasmid pBluescript SK using the method recommended by Stratagene. When the lengths of the cDNA were investigated by agarose gel electrophoresis, insertion of a maximum length of 2.0 kb was observed.

(3) Determination of Nucleotide Sequence

Plasmids were extracted from the resulting clones, and the nucleotide sequences near the 3' and 5' ends of the cDNA were determined according to the dideoxy sequence method using fluorescent reagent as recommended by Perkin-Elmer with the ABI 373A sequencer (Perkin-Elmer). As a result, five of the seven clones had mutually same nucleotide sequences although the lengths of the cDNA were different. The entire nucleotide sequence of pSHGT8 was determined. Determination of nucleotide sequences was performed as described above by either using the Kilo-Sequence Deletion Kit (Takara Shuzo) to obtain a series of deleted cDNA clones, or by using an oligoprimer specific for the internal sequence of pSHGT8.

(4) Comparison of the Nucleotide Sequence and the Amino Acid Sequence

The cDNA inserted into pSHGT8 had the length of 2062 bp, and included an open reading frame (ORF) consisting of 1386 bp in length (including a stop codon). This sequence is shown in SEQ ID NO: 5. The amino acid sequence of this ORF had homology of 68% with the amino acid sequence of *Perilla* 5GT encoded by p3R4, and homology of 64% with that encoded by p3R6. In addition, it also had homology of 22 to 25% with the 3GTs of monocotyledonous and dicotyledoneous plants, and homology of 21% with *petunia* 3RT.

(5) Expression in Yeast and Measurement of Enzymatic Activity

An approximately 2.0 kb DNA fragment obtained by digesting pSHGT8 with BamHI/XhoI, and an approximately 8 kb DNA fragment obtained by digesting pYE22m with BamHI/SalI were ligated, and the resulting plasmid was designated as pYHGT8. pYHGT8 was expressed in yeast cells in the same manner as Example 1, and the enzymatic activity of the protein encoded by pSHGT8 was measured. As a result, in the reaction mixture containing the crude enzyme solution of yeast transformed with pYHGT8, a product was obtained that coincided with cyanidin-3,5-diglucoside in both retention time and absorption spectrum. Based on this observation, the pSHGT8 cDNA of *Verbena* was determined to code for 5GT.

Example 3

Cloning of Trenia 5GT Gene (1) Preparation of cDNA Library

Petals were collected from *torenia* variety *Summer Wave Blue* (Suntory) and ground in a mortar and pestle in liquid nitrogen. RNA was extracted from the ground tissues according to a method using guanidine thiocyanate/cesium chloride, and poly A+RNA was obtained by the method recommended by the manufacturer using Oligotex (Takara Shuzo). The method using guanidine thiocyanate/cesium chloride was carried out in accordance with the method described in detail in Methods in Molecular Biology, Vol. 2 (Humana Press Inc., 1984) by R. McGookin and Robert J. Slater, et al.

Using the resulting poly A+RNA as a template, double-strand cDNA was synthesized using the ZAP-cDNA synthesis kit of Stratagene, then, a cDNA library was prepared using the Uni-ZAP XR Cloning Kit (Stratagene) according to the method recommended by the manufacturer.

(2) Cloning of 5GT cDNA

The λ phage library obtained as described above was screened in the same manner as Example 2 using the p3R4 cDNA of *Perilla* as a probe. As a result, eight positive clones were obtained. After excision of the cDNA on plasmid pBluescript SK, the lengths of the cDNA were investigated by agarose gel electrophoresis, which revealed that a maximum length of insertion was 1.6 kb.

(3) Determination of Nucleotide Sequence

Plasmids were extracted from the resulting clones, and the nucleotide sequences near both 5' and 3' ends were determined in the same manner as Example 2. As a result, six of the eight clones were considered to have mutually same nucleotide sequences although the lengths of the cDNA were different. The entire nucleotide sequence of pSTGT5 cDNA was determined.

(4) Comparison of the Nucleotide Sequence and the Amino Acid Sequence

The cDNA encoded in pSTGT5 was of 1671 bp in length, and included an open reading frame (ORF) consisting of 1437 bp in length (including a stop codon). This sequence is shown in SEQ ID NO: 7. The amino acid sequence of this ORF had homology of 58% with the amino acid sequence of *Perilla* 5GT encoded by p3R4, homology of 57% with that encoded by p3R6, and homology of 57% with that encoded by *Verbena* pSHGT8. In addition, it also had homology of 19 to 23% with the 3GT of monocotyledonous and dicotyledoneous plants, and homology of 20% with *petunia* 3RT.

(5) Expression of 5GT Gene in Yeast

An approximately 1.6 kb DNA fragment obtained by digesting pSTGT5 with SmaI/KpnI, and an approximately 8 kb DNA fragment obtained by blunting the EcoRI-digested site of pYE22m and then digesting with KpnI were ligated, and the resulting plasmid was designated as pYTGT5. pYTGT5 was expressed in yeast cells in the same manner as Example 1, and the enzymatic activity of the protein encoded by pSTGT5 was measured. As a result, in the reaction mixture containing the crude enzyme solution of yeast transformed with pYTGT5, a product was obtained that coincided with cyanidin-3,5-diglucoside in both retention time and absorption spectrum. Based on this observation, the pSTGT5 cDNA of *Torenia* was determined to code for 5GT.

Example 4

Cloning of *Petunia* 5GT Gene (1) Preparation of cDNA Library

A cDNA library was prepared by RNA extracted from petals of the *Petunia* variety Old Glory Blue in the manner described in detail by T. Holton, et al. (Plant Journal, 1993 4: 1003-1010)

(2) Cloning of 5GT cDNA

The cDNA library was screened in the same manner as Example 2 using the mixture of 5GT cDNAs of *Perilla, torenia* and *verbena* obtained in the manner described above as probes. As a result, four positive cDNA clones were obtained and excised on plasmid pBluescript SK. The lengths of the cDNA were investigated by agarose gel electrophoresis, cDNA of a maximum length of 2.0 kb was observed.

(3) Determination of the Nucleotide Sequence

Plasmids were extracted from the resulting clones, and the nucleotide sequence near the 5' end was determined in the same manner as Example 2. As a result, two of the four clones, pSPGT1, were appeared to code an amino acid sequence with a high degree of homology with those of 5GT from *Perilla, torenia* and *verbena* obtained thus far. Therefore, the entire nucleotide sequence of pSPGT1 was determined.

(4) Comparison of the Nucleotide Sequence and the Amino Acid Sequence

The pSPGT1 cDNA was 2015 bp in length, and included an open reading frame (ORF) consisting of 1407 bp (including a stop codon). This sequence is shown in SEQ ID NO: 11. The amino acid sequence of this ORF had homology of 57% with that of 5GT encoded by p3R4 of *Perilla*, homology of 54% with that encoded by p3R6, 55% with that encoded by pSHGT8 of *verbena*, and 51% of that encoded by pTGT5 of *torenia*. In addition, it also had homology of 20 to 29% with the 3GT of monocotyledonous and dicotyledoneous plants, and homology of 20% with *petunia* 3RT. Based on this observation, pSPGT1 cDNA obtained from *petunia* is considered to code for 5GT.

INDUSTRIAL APPLICABILITY

As has been described above, cDNA coding for enzymes that transfer a glycoside to the 5 position of a flavonoid originating in *Perilla, verbena, torenia* and *petunia* were cloned and their nucleotide sequences were determined. In addition, the isolated cDNAs were clearly shown to code for 5GT by the enzymatic activity of their protein expressed in yeast. Introducing of these cDNAs into a suitable plant expression vector and transferring the resulting expression constructs into a plant makes it possible to provide, increase or decrease 5GT activity in the transformed plant, which leads to regulation of flower color. In addition, by using this enzyme, the structure of anthocyans can be altered or more stable anthocyans can be synthesized either in plants or in vitro.

The invention claimed is:

1. An isolated protein having an activity that transfers a glycoside to the 5 position of a flavonoid, wherein said protein comprises a sequence selected from the group consisting of SEQ ID NO: 2, 4, 6, and 8.

2. The isolated protein of claim 1, wherein said protein comprises the sequence of SEQ ID NO: 2.

3. The isolated protein of claim 1, wherein said protein comprises the sequence of SEQ ID NO: 4.

4. The isolated protein of claim 1, wherein said protein comprises the sequence of SEQ ID NO: 6.

5. The isolated protein of claim 1, wherein said protein comprises the sequence of SEQ ID NO: 8.

* * * * *

SEQUENCE LISTING

```
<160> NUMBER OF SEQ ID NOS: 12

<210> SEQ ID NO 1
<211> LENGTH: 1507
<212> TYPE: DNA
<213> ORGANISM: Perilla frutescens
<220> FEATURE:
<221> NAME/KEY: CDS
<222> LOCATION: (17)..(1396)

<400> SEQUENCE: 1
gaaaatttcc acaaaa atg gtc cgc cgc cgc gtg ctg cta gca acg ttt cct      52
               Met Val Arg Arg Arg Val Leu Leu Ala Thr Phe Pro
                 1               5                  10 gcg caa ggc cac ata aat ccc gcc ctc caa ttc gcc aag aga ctc cta       100
Ala Gln Gly His Ile Asn Pro Ala Leu Gln Phe Ala Lys Arg Leu Leu
         15                  20                  25 aaa gcc ggc act gac gtc aca ttt ttc acg agc gtt tat gca tgg cgc       148
Lys Ala Gly Thr Asp Val Thr Phe Phe Thr Ser Val Tyr Ala Trp Arg
     30                  35                  40 cgc atg gcc aac aca gcc tcc gcc gct gcc gga aac cca ccg ggc ctc       196
Arg Met Ala Asn Thr Ala Ser Ala Ala Ala Gly Asn Pro Pro Gly Leu
 45                  50                  55                  60 gac ttc gtg gcg ttc tcc gac ggc tac gac gac ggg ctg aag ccc tgc       244
Asp Phe Val Ala Phe Ser Asp Gly Tyr Asp Asp Gly Leu Lys Pro Cys
                 65                  70                  75
```

-continued

| | |
|---|---|
| ggc gac ggg aag cgc tac atg tcc gag atg aaa gcc cgc ggc tcc gag<br>Gly Asp Gly Lys Arg Tyr Met Ser Glu Met Lys Ala Arg Gly Ser Glu<br>           80                   85                   90 | 292 |
| gcc tta aga aac ctc ctt ctc aac aac cac gac gtc acg ttc gtc gtc<br>Ala Leu Arg Asn Leu Leu Leu Asn Asn His Asp Val Thr Phe Val Val<br>          95                 100                105 | 340 |
| tac tcc cac ctc ttt gca tgg gcg gcg gag gtg gcg cgt gag tcc cag<br>Tyr Ser His Leu Phe Ala Trp Ala Ala Glu Val Ala Arg Glu Ser Gln<br>   110                  115                120 | 388 |
| gtc ccg agc gcc ctt ctc tgg gtc gag ccc gcc acc gtg ctg tgc ata<br>Val Pro Ser Ala Leu Leu Trp Val Glu Pro Ala Thr Val Leu Cys Ile<br>125               130                135              140 | 436 |
| tat tac ttc tac ttc aac ggc tac gca gac gag atc gac gcc ggt tcc<br>Tyr Tyr Phe Tyr Phe Asn Gly Tyr Ala Asp Glu Ile Asp Ala Gly Ser<br>               145                150              155 | 484 |
| gac gaa att cag ctc cct cgg ctt cca ccc ctg gag cag cgc agt ctt<br>Asp Glu Ile Gln Leu Pro Arg Leu Pro Pro Leu Glu Gln Arg Ser Leu<br>                   160                165              170 | 532 |
| ccg acc ttt ctg ctg ccg gag aca ccg gag aga ttc cgg ttg atg atg<br>Pro Thr Phe Leu Leu Pro Glu Thr Pro Glu Arg Phe Arg Leu Met Met<br>               175                180              185 | 580 |
| aag gag aag ctg gaa act tta gac ggt gaa gag aag gcg aaa gtg ttg<br>Lys Glu Lys Leu Glu Thr Leu Asp Gly Glu Glu Lys Ala Lys Val Leu<br>   190                  195                200 | 628 |
| gtg aac acg ttt gat gcg ttg gag ccc gat gca ctc acg gct att gat<br>Val Asn Thr Phe Asp Ala Leu Glu Pro Asp Ala Leu Thr Ala Ile Asp<br>205               210                215              220 | 676 |
| agg tat gag ttg atc ggg atc ggg ccg ttg att ccc tcc gcc ttc ttg<br>Arg Tyr Glu Leu Ile Gly Ile Gly Pro Leu Ile Pro Ser Ala Phe Leu<br>                   225                230              235 | 724 |
| gac ggc gga gat ccc tcc gaa acg tct tac ggc ggc gat ctt ttc gaa<br>Asp Gly Gly Asp Pro Ser Glu Thr Ser Tyr Gly Gly Asp Leu Phe Glu<br>                   240                245              250 | 772 |
| aaa tcg gag gag aat aac tgc gtg gag tgg ttg gac acg aag ccg aaa<br>Lys Ser Glu Glu Asn Asn Cys Val Glu Trp Leu Asp Thr Lys Pro Lys<br>           255                260              265 | 820 |
| tct tcg gtg gtg tat gtg tcg ttt ggg agc gtt ttg agg ttt cca aag<br>Ser Ser Val Val Tyr Val Ser Phe Gly Ser Val Leu Arg Phe Pro Lys<br>          270                275              280 | 868 |
| gca caa atg gaa gag att ggg aaa ggg cta tta gcc tgc gga agg ccg<br>Ala Gln Met Glu Glu Ile Gly Lys Gly Leu Leu Ala Cys Gly Arg Pro<br>285               290                295              300 | 916 |
| ttt tta tgg atg ata cga gaa cag aag aat gac gac ggc gaa gaa gaa<br>Phe Leu Trp Met Ile Arg Glu Gln Lys Asn Asp Asp Gly Glu Glu Glu<br>               305                310              315 | 964 |
| gaa gaa gag ttg agt tgc att ggg gaa ttg aaa aaa atg ggg aaa ata<br>Glu Glu Glu Leu Ser Cys Ile Gly Glu Leu Lys Lys Met Gly Lys Ile<br>               320                325              330 | 1012 |
| gtt tcg tgg tgc tcg cag ttg gag gtt ctg gcg cac cct gcg ttg gga<br>Val Ser Trp Cys Ser Gln Leu Glu Val Leu Ala His Pro Ala Leu Gly<br>          335                340              345 | 1060 |
| tgt ttc gtg acg cat tgt ggg tgg aac tcg gct gtg gag agc ttg agt<br>Cys Phe Val Thr His Cys Gly Trp Asn Ser Ala Val Glu Ser Leu Ser<br>   350                  355                360 | 1108 |
| tgc ggg gtt ccg gtg gtg gcg gtg ccg cag tgg ttt gat cag acg acg<br>Cys Gly Val Pro Val Val Ala Val Pro Gln Trp Phe Asp Gln Thr Thr<br>365               370                375              380 | 1156 |
| aat gcg aag ctg att gag gat gcg tgg ggg aca ggg gtg aga gtg aga<br>Asn Ala Lys Leu Ile Glu Asp Ala Trp Gly Thr Gly Val Arg Val Arg<br>                   385                390              395 | 1204 |

-continued

```
atg aat gaa ggg ggt ggg gtt gat gga tct gag ata gag agg tgt gtg     1252
Met Asn Glu Gly Gly Gly Val Asp Gly Ser Glu Ile Glu Arg Cys Val
        400                 405                 410 gag atg gtg atg gat ggg ggt gag aag agc aaa cta gtg aga gaa aat     1300
Glu Met Val Met Asp Gly Gly Glu Lys Ser Lys Leu Val Arg Glu Asn
    415                 420                 425 gcc ata aaa tgg aag act ttg gcc aga gaa gcc atg gga gag gat gga     1348
Ala Ile Lys Trp Lys Thr Leu Ala Arg Glu Ala Met Gly Glu Asp Gly
430                 435                 440 tct tca ctc aag aat ctc aac gcc ttt ctt cat caa gtt gca cgt gct     1396
Ser Ser Leu Lys Asn Leu Asn Ala Phe Leu His Gln Val Ala Arg Ala
445                 450                 455                 460 taatacacaa aatggctttc cacttttaat ctactcaaac accggttcaa ataaatatcc   1456
ccttccactt ctttctattt cactatcaca tttataattt tagtaacaaa a            1507

<210> SEQ ID NO 2
<211> LENGTH: 460
<212> TYPE: PRT
<213> ORGANISM: Perilla frutescens

<400> SEQUENCE: 2

Met Val Arg Arg Val Leu Leu Ala Thr Phe Pro Ala Gln Gly His
  1               5                  10                  15

Ile Asn Pro Ala Leu Gln Phe Ala Lys Arg Leu Leu Lys Ala Gly Thr
             20                  25                  30

Asp Val Thr Phe Phe Thr Ser Val Tyr Ala Trp Arg Arg Met Ala Asn
         35                  40                  45

Thr Ala Ser Ala Ala Ala Gly Asn Pro Pro Gly Leu Asp Phe Val Ala
     50                  55                  60

Phe Ser Asp Gly Tyr Asp Asp Gly Leu Lys Pro Cys Gly Asp Gly Lys
 65                  70                  75                  80

Arg Tyr Met Ser Glu Met Lys Ala Arg Gly Ser Glu Ala Leu Arg Asn
                 85                  90                  95

Leu Leu Leu Asn Asn His Asp Val Thr Phe Val Val Tyr Ser His Leu
            100                 105                 110

Phe Ala Trp Ala Ala Glu Val Ala Arg Glu Ser Gln Val Pro Ser Ala
        115                 120                 125

Leu Leu Trp Val Glu Pro Ala Thr Val Leu Cys Ile Tyr Tyr Phe Tyr
    130                 135                 140

Phe Asn Gly Tyr Ala Asp Glu Ile Asp Ala Gly Ser Asp Glu Ile Gln
145                 150                 155                 160

Leu Pro Arg Leu Pro Pro Leu Glu Gln Arg Ser Leu Pro Thr Phe Leu
                165                 170                 175

Leu Pro Glu Thr Pro Glu Arg Phe Arg Leu Met Met Lys Glu Lys Leu
            180                 185                 190

Glu Thr Leu Asp Gly Glu Glu Lys Ala Lys Val Leu Val Asn Thr Phe
        195                 200                 205

Asp Ala Leu Glu Pro Asp Ala Leu Thr Ala Ile Asp Arg Tyr Glu Leu
    210                 215                 220

Ile Gly Ile Gly Pro Leu Ile Pro Ser Ala Phe Leu Asp Gly Asp
225                 230                 235                 240

Pro Ser Glu Thr Ser Tyr Gly Gly Asp Leu Phe Glu Lys Ser Glu Glu
                245                 250                 255

Asn Asn Cys Val Glu Trp Leu Asp Thr Lys Pro Lys Ser Ser Val Val
            260                 265                 270
```

```
Tyr Val Ser Phe Gly Ser Val Leu Arg Phe Pro Lys Ala Gln Met Glu
        275                 280                 285

Glu Ile Gly Lys Gly Leu Leu Ala Cys Gly Arg Pro Phe Leu Trp Met
    290                 295                 300

Ile Arg Glu Gln Lys Asn Asp Asp Gly Glu Glu Glu Glu Glu Glu Leu
305                 310                 315                 320

Ser Cys Ile Gly Glu Leu Lys Lys Met Gly Lys Ile Val Ser Trp Cys
                325                 330                 335

Ser Gln Leu Glu Val Leu Ala His Pro Ala Leu Gly Cys Phe Val Thr
            340                 345                 350

His Cys Gly Trp Asn Ser Ala Val Glu Ser Leu Ser Cys Gly Val Pro
        355                 360                 365

Val Val Ala Val Pro Gln Trp Phe Asp Gln Thr Thr Asn Ala Lys Leu
    370                 375                 380

Ile Glu Asp Ala Trp Gly Thr Gly Val Arg Val Arg Met Asn Glu Gly
385                 390                 395                 400

Gly Gly Val Asp Gly Ser Glu Ile Glu Arg Cys Val Glu Met Val Met
                405                 410                 415

Asp Gly Gly Glu Lys Ser Lys Leu Val Arg Glu Asn Ala Ile Lys Trp
            420                 425                 430

Lys Thr Leu Ala Arg Glu Ala Met Gly Glu Asp Gly Ser Ser Leu Lys
        435                 440                 445

Asn Leu Asn Ala Phe Leu His Gln Val Ala Arg Ala
    450                 455                 460

<210> SEQ ID NO 3
<211> LENGTH: 1474
<212> TYPE: DNA
<213> ORGANISM: Perilla frutescens
<220> FEATURE:
<221> NAME/KEY: CDS
<222> LOCATION: (29)..(1357)

<400> SEQUENCE: 3
accaaaccaa aacaaaattt ccacaaaa atg gtc cgc cgc cgc gtg ctg cta        52
                                Met Val Arg Arg Arg Val Leu Leu
                                  1               5 gca acg ttt ccg gcg caa ggc cac ata aat ccc gcc ctc caa ttc gcc      100
Ala Thr Phe Pro Ala Gln Gly His Ile Asn Pro Ala Leu Gln Phe Ala
         10                  15                  20 aag aga ctc cta aaa gcc ggc act gac gtc acg ttt ttc acg agc gtt      148
Lys Arg Leu Leu Lys Ala Gly Thr Asp Val Thr Phe Phe Thr Ser Val
 25                  30                  35                  40 tat gca tgg cgc cgc atg gcc aac aca gcc tcc gcc gct gcc gga aac      196
Tyr Ala Trp Arg Arg Met Ala Asn Thr Ala Ser Ala Ala Ala Gly Asn
                 45                  50                  55 cca ccg ggc ctc gac ttc gtg gcg ttc tcc gac ggc tac gac gac ggg      244
Pro Pro Gly Leu Asp Phe Val Ala Phe Ser Asp Gly Tyr Asp Asp Gly
             60                  65                  70 ctg aag ccc ggc ggc gac ggg aag cgc tac atg tcc gag atg aaa gcc      292
Leu Lys Pro Gly Gly Asp Gly Lys Arg Tyr Met Ser Glu Met Lys Ala
         75                  80                  85 cgc ggc tcc gag gcc tta aga aac ctc ctt ctc aac aac gac gac gtc      340
Arg Gly Ser Glu Ala Leu Arg Asn Leu Leu Leu Asn Asn Asp Asp Val
 90                  95                 100 act ttc gtc gtc tac tcc cac ctc ttt gca tgg gcg gcg gag gtg gcg      388
Thr Phe Val Val Tyr Ser His Leu Phe Ala Trp Ala Ala Glu Val Ala
105                 110                 115                 120
```

```
cgt ttg tcc cac gtc ccg acc gcc ctt ctc tgg gtc gag ccc gcc acc         436
Arg Leu Ser His Val Pro Thr Ala Leu Leu Trp Val Glu Pro Ala Thr
            125                 130                 135 gtg ctg tgc ata tac cac ttc tac ttc aac ggc tac gca gac gag atc         484
Val Leu Cys Ile Tyr His Phe Tyr Phe Asn Gly Tyr Ala Asp Glu Ile
        140                 145                 150 gac gcc ggt tcc aat gaa att cag ctc cct cgg ctt cca tcc ctg gag         532
Asp Ala Gly Ser Asn Glu Ile Gln Leu Pro Arg Leu Pro Ser Leu Glu
                155                 160                 165 cag cgc agt ctt ccg acg ttt ctg ctg cct gcg acg ccg gag aga ttc         580
Gln Arg Ser Leu Pro Thr Phe Leu Leu Pro Ala Thr Pro Glu Arg Phe
    170                 175                 180 cgg ttg atg atg aag gag aag ctg gaa act tta gac ggt gaa gag aag         628
Arg Leu Met Met Lys Glu Lys Leu Glu Thr Leu Asp Gly Glu Glu Lys
185                 190                 195                 200 gcg aaa gta ttg gtg aac acg ttt gat gcg ttg gag ccc gat gca ctc         676
Ala Lys Val Leu Val Asn Thr Phe Asp Ala Leu Glu Pro Asp Ala Leu
                205                 210                 215 acg gct att gat agg tat gag ttg atc ggg atc ggg ccg ttg att ccc         724
Thr Ala Ile Asp Arg Tyr Glu Leu Ile Gly Ile Gly Pro Leu Ile Pro
        220                 225                 230 tcc gcc ttc ttg gac ggc gaa gat ccc tcc gaa acg tct tac ggc ggc         772
Ser Ala Phe Leu Asp Gly Glu Asp Pro Ser Glu Thr Ser Tyr Gly Gly
                235                 240                 245 gat ctt ttc gaa aaa tcg gag gag aat aac tgc gtg gag tgg ttg aac         820
Asp Leu Phe Glu Lys Ser Glu Glu Asn Asn Cys Val Glu Trp Leu Asn
    250                 255                 260 tcg aag ccg aaa tct tcg gtg gtg tat gtg tcg ttt ggg agc gtt ttg         868
Ser Lys Pro Lys Ser Ser Val Val Tyr Val Ser Phe Gly Ser Val Leu
265                 270                 275                 280 agg ttt cca aag gca caa atg gaa gag att ggg aaa ggg cta tta gcc         916
Arg Phe Pro Lys Ala Gln Met Glu Glu Ile Gly Lys Gly Leu Leu Ala
                285                 290                 295 tgc gga agg ccc ttt tta tgg atg ata cga gaa cag aag aat gac gac         964
Cys Gly Arg Pro Phe Leu Trp Met Ile Arg Glu Gln Lys Asn Asp Asp
        300                 305                 310 ggc gaa gaa gaa gaa gaa gaa gag ttg agt tgc att ggg gaa ttg                1012
Gly Glu Glu Glu Glu Glu Glu Glu Leu Ser Cys Ile Gly Glu Leu
                315                 320                 325 aaa aaa atg ggg aaa ata gtg tcg tgg tgc tcg cag ttg gag gtt ctg         1060
Lys Lys Met Gly Lys Ile Val Ser Trp Cys Ser Gln Leu Glu Val Leu
    330                 335                 340 gcg cac cct gcg ttg gga tgt ttc gtg acg cat tgt ggg tgg aac tcg         1108
Ala His Pro Ala Leu Gly Cys Phe Val Thr His Cys Gly Trp Asn Ser
345                 350                 355                 360 gct gtg gag agc ttg agt tgc ggg att ccg gtg gtg gcg gtg ccg cag         1156
Ala Val Glu Ser Leu Ser Cys Gly Ile Pro Val Val Ala Val Pro Gln
                365                 370                 375 tgg ttt gat cag acg acg aat gcg aag ctg att gag gat gcg tgg ggg         1204
Trp Phe Asp Gln Thr Thr Asn Ala Lys Leu Ile Glu Asp Ala Trp Gly
        380                 385                 390 aca ggg gtg aga gtg aga atg aat gaa ggg ggt ggg gtt gat gga tgt         1252
Thr Gly Val Arg Val Arg Met Asn Glu Gly Gly Gly Val Asp Gly Cys
            395                 400                 405 gag ata gaa agg tgt gtg gag atg gtg atg gat ggg ggt gac aag acc         1300
Glu Ile Glu Arg Cys Val Glu Met Val Met Asp Gly Gly Asp Lys Thr
                410                 415                 420 aaa cta gtg aga gaa aat gcc atc aaa tgg aag act ttg gcc aga caa         1348
Lys Leu Val Arg Glu Asn Ala Ile Lys Trp Lys Thr Leu Ala Arg Gln
425                 430                 435                 440
```

```
gcc atg gga taggatggat cttcactcaa caatctcaac gcctttcttc         1397
Ala Met Gly gtcaagttgc acactttaa tctgctcaaa cagcggttca aataaatatc cccttccact  1457
taaaaaaaaa aaaaaaa                                                1474
```

```
<210> SEQ ID NO 4
<211> LENGTH: 443
<212> TYPE: PRT
<213> ORGANISM: Perilla frutescens

<400> SEQUENCE: 4
```

```
Met Val Arg Arg Arg Val Leu Leu Ala Thr Phe Pro Ala Gln Gly His
 1               5                  10                  15

Ile Asn Pro Ala Leu Gln Phe Ala Lys Arg Leu Leu Lys Ala Gly Thr
             20                  25                  30

Asp Val Thr Phe Phe Thr Ser Val Tyr Ala Trp Arg Arg Met Ala Asn
         35                  40                  45

Thr Ala Ser Ala Ala Ala Gly Asn Pro Pro Gly Leu Asp Phe Val Ala
     50                  55                  60

Phe Ser Asp Gly Tyr Asp Asp Gly Leu Lys Pro Gly Gly Asp Gly Lys
 65                  70                  75                  80

Arg Tyr Met Ser Glu Met Lys Ala Arg Gly Ser Glu Ala Leu Arg Asn
                 85                  90                  95

Leu Leu Leu Asn Asn Asp Asp Val Thr Phe Val Val Tyr Ser His Leu
            100                 105                 110

Phe Ala Trp Ala Ala Glu Val Ala Arg Leu Ser His Val Pro Thr Ala
        115                 120                 125

Leu Leu Trp Val Glu Pro Ala Thr Val Leu Cys Ile Tyr His Phe Tyr
    130                 135                 140

Phe Asn Gly Tyr Ala Asp Glu Ile Asp Ala Gly Ser Asn Glu Ile Gln
145                 150                 155                 160

Leu Pro Arg Leu Pro Ser Leu Glu Gln Arg Ser Leu Pro Thr Phe Leu
                165                 170                 175

Leu Pro Ala Thr Pro Glu Arg Phe Arg Leu Met Met Lys Glu Lys Leu
            180                 185                 190

Glu Thr Leu Asp Gly Glu Glu Lys Ala Lys Val Leu Val Asn Thr Phe
        195                 200                 205

Asp Ala Leu Glu Pro Asp Ala Leu Thr Ala Ile Asp Arg Tyr Glu Leu
    210                 215                 220

Ile Gly Ile Gly Pro Leu Ile Pro Ser Ala Phe Leu Asp Gly Glu Asp
225                 230                 235                 240

Pro Ser Glu Thr Ser Tyr Gly Gly Asp Leu Phe Glu Lys Ser Glu Glu
                245                 250                 255

Asn Asn Cys Val Glu Trp Leu Asn Ser Lys Pro Lys Ser Ser Val Val
            260                 265                 270

Tyr Val Ser Phe Gly Ser Val Leu Arg Phe Pro Lys Ala Gln Met Glu
        275                 280                 285

Glu Ile Gly Lys Gly Leu Leu Ala Cys Gly Arg Pro Phe Leu Trp Met
    290                 295                 300

Ile Arg Glu Gln Lys Asn Asp Asp Gly Glu Glu Glu Glu Glu Glu Glu
305                 310                 315                 320

Glu Leu Ser Cys Ile Gly Glu Leu Lys Lys Met Gly Lys Ile Val Ser
                325                 330                 335
```

```
Trp Cys Ser Gln Leu Glu Val Leu Ala His Pro Ala Leu Gly Cys Phe
            340                 345                 350
Val Thr His Cys Gly Trp Asn Ser Ala Val Glu Ser Leu Ser Cys Gly
            355                 360                 365
Ile Pro Val Val Ala Val Pro Gln Trp Phe Asp Gln Thr Thr Asn Ala
        370                 375                 380
Lys Leu Ile Glu Asp Ala Trp Gly Thr Gly Val Arg Val Arg Met Asn
385                 390                 395                 400
Glu Gly Gly Gly Val Asp Gly Cys Glu Ile Glu Arg Cys Val Glu Met
                405                 410                 415
Val Met Asp Gly Gly Asp Lys Thr Lys Leu Val Arg Glu Asn Ala Ile
            420                 425                 430
Lys Trp Lys Thr Leu Ala Arg Gln Ala Met Gly
            435                 440

<210> SEQ ID NO 5
<211> LENGTH: 2062
<212> TYPE: DNA
<213> ORGANISM: Verbena hybrida
<220> FEATURE:
<221> NAME/KEY: CDS
<222> LOCATION: (26)..(1408)

<400> SEQUENCE: 5
attttaccaa aaaataaaa aaaaa atg agc aga gct cac gtc ctc ttg gcc      52
                          Met Ser Arg Ala His Val Leu Leu Ala
                           1               5 aca ttc cca gca cag gga cac ata aat ccc gcc ctt caa ttc gcc aag   100
Thr Phe Pro Ala Gln Gly His Ile Asn Pro Ala Leu Gln Phe Ala Lys
 10              15                  20                  25 cgt ctc gca aat gcc gac att caa gtc aca ttc ttc acc agc gtc tac   148
Arg Leu Ala Asn Ala Asp Ile Gln Val Thr Phe Phe Thr Ser Val Tyr
             30                  35                  40 gca tgg cgc cgc atg tcc aga acc gcc gct ggc tca aac ggg ctc atc   196
Ala Trp Arg Arg Met Ser Arg Thr Ala Ala Gly Ser Asn Gly Leu Ile
         45                  50                  55 aat ttt gtg tcg ttt tcc gac ggg tat gac gac ggg tta cag ccc gga   244
Asn Phe Val Ser Phe Ser Asp Gly Tyr Asp Asp Gly Leu Gln Pro Gly
     60                  65                  70 gac gat ggg aag aac tac atg tcg gag atg aaa agc aga ggt ata aaa   292
Asp Asp Gly Lys Asn Tyr Met Ser Glu Met Lys Ser Arg Gly Ile Lys
 75                  80                  85 gcc ttg agc gat act ctt gca gcc aat aat gtc gat caa aaa agc agc   340
Ala Leu Ser Asp Thr Leu Ala Ala Asn Asn Val Asp Gln Lys Ser Ser
 90                  95                 100                 105 aaa atc acg ttc gtg gtg tac tcc cac ctc ttt gca tgg gcg gcc aag   388
Lys Ile Thr Phe Val Val Tyr Ser His Leu Phe Ala Trp Ala Ala Lys
             110                 115                 120 gtg gcg cgt gag ttc cat ctc cgg agc gcg cta ctc tgg att gag cca   436
Val Ala Arg Glu Phe His Leu Arg Ser Ala Leu Leu Trp Ile Glu Pro
         125                 130                 135 gct acg gtg ttg gat ata ttt tac ttt tat ttc aac ggc tat agc gac   484
Ala Thr Val Leu Asp Ile Phe Tyr Phe Tyr Phe Asn Gly Tyr Ser Asp
     140                 145                 150 gaa atc gat gcg ggt tcg gat gct att cac ttg ccc gga gga ctc cca   532
Glu Ile Asp Ala Gly Ser Asp Ala Ile His Leu Pro Gly Gly Leu Pro
 155                 160                 165 gtg ctg gcc cag cgt gat tta ccg tct ttc ctt ctt cct tcc acg cat   580
Val Leu Ala Gln Arg Asp Leu Pro Ser Phe Leu Leu Pro Ser Thr His
170                 175                 180                 185
```

```
gag aga ttc cgt tca ctg atg aag gag aaa ttg gaa act tta gaa ggt    628
Glu Arg Phe Arg Ser Leu Met Lys Glu Lys Leu Glu Thr Leu Glu Gly
            190                 195                 200 gaa gaa aaa cct aag gtc ttg gtg aac agc ttt gat gcg ttg gag cct    676
Glu Glu Lys Pro Lys Val Leu Val Asn Ser Phe Asp Ala Leu Glu Pro
            205                 210                 215 gat gcg ctc aag gcc att gat aag tac gag atg att gca atc ggg ccg    724
Asp Ala Leu Lys Ala Ile Asp Lys Tyr Glu Met Ile Ala Ile Gly Pro
            220                 225                 230 ttg att cct tcc gca ttc ttg gac ggt aaa gat cct tcg gac agg tct    772
Leu Ile Pro Ser Ala Phe Leu Asp Gly Lys Asp Pro Ser Asp Arg Ser
        235                 240                 245 ttc ggc gga gat ttg ttc gag aaa ggg tcg aat gac gac gat tgc ctc    820
Phe Gly Gly Asp Leu Phe Glu Lys Gly Ser Asn Asp Asp Asp Cys Leu
250                 255                 260                 265 gaa tgg ttg agc acg aat cct cga tct tcg gtg gtt tac gtt tcg ttc    868
Glu Trp Leu Ser Thr Asn Pro Arg Ser Ser Val Val Tyr Val Ser Phe
                270                 275                 280 gga agc ttc gtt aat acg acg aag tcg caa atg gaa gag ata gca aga    916
Gly Ser Phe Val Asn Thr Thr Lys Ser Gln Met Glu Glu Ile Ala Arg
            285                 290                 295 ggg ctg tta gat tgt ggg agg ccg ttt ttg tgg gta gta aga gta aac    964
Gly Leu Leu Asp Cys Gly Arg Pro Phe Leu Trp Val Val Arg Val Asn
        300                 305                 310 gaa gga gaa gag gta ttg ata agt tgc atg gag gag ttg aaa cga gtg    1012
Glu Gly Glu Glu Val Leu Ile Ser Cys Met Glu Glu Leu Lys Arg Val
            315                 320                 325 ggg aaa att gta tct tgg tgt tct caa ttg gaa gtc ctg acg cat ccc    1060
Gly Lys Ile Val Ser Trp Cys Ser Gln Leu Glu Val Leu Thr His Pro
330                 335                 340                 345 tcg ttg gga tgt ttc gtg aca cac tgc ggg tgg aat tcg act cta gag    1108
Ser Leu Gly Cys Phe Val Thr His Cys Gly Trp Asn Ser Thr Leu Glu
                350                 355                 360 agt ata tct ttc ggg gtt ccg atg gtg gct ttt ccg cag tgg ttc gat    1156
Ser Ile Ser Phe Gly Val Pro Met Val Ala Phe Pro Gln Trp Phe Asp
            365                 370                 375 caa ggg acg aat gcg aag ctg atg gag gat gtg tgg agg acg ggt gtg    1204
Gln Gly Thr Asn Ala Lys Leu Met Glu Asp Val Trp Arg Thr Gly Val
        380                 385                 390 aga gtg aga gct aat gag gag ggt agc gtc gtt gat ggt gat gaa att    1252
Arg Val Arg Ala Asn Glu Glu Gly Ser Val Val Asp Gly Asp Glu Ile
    395                 400                 405 agg aga tgt att gag gag gtt atg gat ggg gga gaa aag agt agg aaa    1300
Arg Arg Cys Ile Glu Glu Val Met Asp Gly Gly Glu Lys Ser Arg Lys
410                 415                 420                 425 ctt aga gag agt gct ggc aag tgg aag gat ttg gca aga aaa gct atg    1348
Leu Arg Glu Ser Ala Gly Lys Trp Lys Asp Leu Ala Arg Lys Ala Met
                430                 435                 440 gag gaa gat gga tct tca gtt aac aac ctc aag gtc ttt ctt gat gag    1396
Glu Glu Asp Gly Ser Ser Val Asn Asn Leu Lys Val Phe Leu Asp Glu
            445                 450                 455 gtt gta ggt atc taaagacgta aatgaggtcc ccataggcaa aattgcaaat        1448
Val Val Gly Ile
        460 ttcatctcgt aagttgaata cttttggct ttaattttgt tcgagtttgt ttttcaaaat   1508 ttatcttgta attttacatt gagtgtaaat ttagtctgat tttaactgga aaaatataaa  1568 attcattgtt gagactcttc atcaaaatca tctgatttcc tttattgtct tggtcaaaat  1628 tctcatatca attggaaaaa ataaatttca aaatcgtcca attttgaacc aagaaagaag  1688
```

```
tataatttga ccaaaataat aaaaggattc aagtgatctt gatgaagtgt ctgagcgacg    1748
agttctatat ttttccaccg aatttctaac gagttttttga attttttta gccaaaatcg    1808 gactaacttt gtacaaaatg aaaagttata tgatgaaatt ttaaaaaaca aactcagaca    1868
ataataaagc ccgaaagtag taaaattacc tgacgaaatt tgcaatttcg cctcctattt    1928
taattttttt ggtgtgttta ataaatcggt tattttactt ttaattaaaa taaaagtgag    1988
atgcatgata gcttggtgag tatatatgag ttgatggtaa tgtacgatat tttctaaaaa    2048
aaaaaaaaaa aaaa                                                      2062
```

<210> SEQ ID NO 6
<211> LENGTH: 461
<212> TYPE: PRT
<213> ORGANISM: Verbena hybrida

<400> SEQUENCE: 6

```
Met Ser Arg Ala His Val Leu Leu Ala Thr Phe Pro Ala Gln Gly His
  1               5                  10                  15

Ile Asn Pro Ala Leu Gln Phe Ala Lys Arg Leu Ala Asn Ala Asp Ile
                 20                  25                  30

Gln Val Thr Phe Phe Thr Ser Val Tyr Ala Trp Arg Arg Met Ser Arg
             35                  40                  45

Thr Ala Ala Gly Ser Asn Gly Leu Ile Asn Phe Val Ser Phe Ser Asp
         50                  55                  60

Gly Tyr Asp Asp Gly Leu Gln Pro Gly Asp Asp Gly Lys Asn Tyr Met
 65                  70                  75                  80

Ser Glu Met Lys Ser Arg Gly Ile Lys Ala Leu Ser Asp Thr Leu Ala
                 85                  90                  95

Ala Asn Asn Val Asp Gln Lys Ser Ser Lys Ile Thr Phe Val Val Tyr
                100                 105                 110

Ser His Leu Phe Ala Trp Ala Ala Lys Val Ala Arg Glu Phe His Leu
            115                 120                 125

Arg Ser Ala Leu Leu Trp Ile Glu Pro Ala Thr Val Leu Asp Ile Phe
        130                 135                 140

Tyr Phe Tyr Phe Asn Gly Tyr Ser Asp Glu Ile Asp Ala Gly Ser Asp
145                 150                 155                 160

Ala Ile His Leu Pro Gly Gly Leu Pro Val Leu Ala Gln Arg Asp Leu
                165                 170                 175

Pro Ser Phe Leu Leu Pro Ser Thr His Glu Arg Phe Arg Ser Leu Met
            180                 185                 190

Lys Glu Lys Leu Glu Thr Leu Glu Gly Glu Glu Lys Pro Lys Val Leu
        195                 200                 205

Val Asn Ser Phe Asp Ala Leu Glu Pro Asp Ala Leu Lys Ala Ile Asp
    210                 215                 220

Lys Tyr Glu Met Ile Ala Ile Gly Pro Leu Ile Pro Ser Ala Phe Leu
225                 230                 235                 240

Asp Gly Lys Asp Pro Ser Asp Arg Ser Phe Gly Gly Asp Leu Phe Glu
                245                 250                 255

Lys Gly Ser Asn Asp Asp Asp Cys Leu Glu Trp Leu Ser Thr Asn Pro
            260                 265                 270

Arg Ser Ser Val Val Tyr Val Ser Phe Gly Ser Phe Val Asn Thr Thr
        275                 280                 285

Lys Ser Gln Met Glu Glu Ile Ala Arg Gly Leu Leu Asp Cys Gly Arg
    290                 295                 300
```

```
Pro Phe Leu Trp Val Val Arg Val Asn Glu Gly Glu Glu Val Leu Ile
305                 310                 315                 320

Ser Cys Met Glu Glu Leu Lys Arg Val Gly Lys Ile Val Ser Trp Cys
            325                 330                 335

Ser Gln Leu Glu Val Leu Thr His Pro Ser Leu Gly Cys Phe Val Thr
            340                 345                 350

His Cys Gly Trp Asn Ser Thr Leu Glu Ser Ile Ser Phe Gly Val Pro
            355                 360                 365

Met Val Ala Phe Pro Gln Trp Phe Asp Gln Gly Thr Asn Ala Lys Leu
            370                 375                 380

Met Glu Asp Val Trp Arg Thr Gly Val Arg Val Arg Ala Asn Glu Glu
385                 390                 395                 400

Gly Ser Val Val Asp Gly Asp Glu Ile Arg Arg Cys Ile Glu Glu Val
                405                 410                 415

Met Asp Gly Gly Glu Lys Ser Arg Lys Leu Arg Glu Ser Ala Gly Lys
            420                 425                 430

Trp Lys Asp Leu Ala Arg Lys Ala Met Glu Glu Asp Gly Ser Ser Val
            435                 440                 445

Asn Asn Leu Lys Val Phe Leu Asp Glu Val Val Gly Ile
            450                 455                 460

<210> SEQ ID NO 7
<211> LENGTH: 1671
<212> TYPE: DNA
<213> ORGANISM: Torenia hybrira
<220> FEATURE:
<221> NAME/KEY: CDS
<222> LOCATION: (45)..(1478)
<220> FEATURE:
<221> NAME/KEY: misc_feature
<222> LOCATION: (64)
<223> OTHER INFORMATION: Amino acid 64 is Xaa wherein Xaa = Cys or Phe.
<220> FEATURE:
<221> NAME/KEY: misc_feature
<222> LOCATION: (65)
<223> OTHER INFORMATION: Amino acid 65 is Xaa wherein Xaa = Ser or Pro.

<400> SEQUENCE: 7
aacacataaa aaaaaaataa aagaagaaat aattaaaaaa aaaa atg gtt aac aaa        56
                                                 Met Val Asn Lys
                                                  1 cgc cat att cta cta gca aca ttc cca gca caa ggc cac ata aac cct       104
Arg His Ile Leu Leu Ala Thr Phe Pro Ala Gln Gly His Ile Asn Pro
 5                  10                  15                  20 tct ctc gag ttc gcc aaa agg ctc ctc aac acc gga tac gtc gac caa       152
Ser Leu Glu Phe Ala Lys Arg Leu Leu Asn Thr Gly Tyr Val Asp Gln
                25                  30                  35 gtc aca ttc ttc acg agt gta tac gca ttg aga cgc atg cgc ttc gaa       200
Val Thr Phe Phe Thr Ser Val Tyr Ala Leu Arg Arg Met Arg Phe Glu
            40                  45                  50 acc gat ccg agc agc aga atc gat ttc gtg gca tkt yca gat tct tac       248
Thr Asp Pro Ser Ser Arg Ile Asp Phe Val Ala Xaa Xaa Asp Ser Tyr
        55                  60                  65 gat gat ggc tta aag aaa ggc gac gat ggc aaa aac tac atg tcg gag       296
Asp Asp Gly Leu Lys Lys Gly Asp Asp Gly Lys Asn Tyr Met Ser Glu
    70                  75                  80 atg aga aag cgc gga acg aag gcc tta aag gac act ctt att aag ctc       344
Met Arg Lys Arg Gly Thr Lys Ala Leu Lys Asp Thr Leu Ile Lys Leu
85                  90                  95                 100
```

| | | |
|---|---|---|
| aac gat gct gcg atg gga agt gaa tgt tac aat cgc gtg agc ttt gtg<br>Asn Asp Ala Ala Met Gly Ser Glu Cys Tyr Asn Arg Val Ser Phe Val<br>　　　　　　　105　　　　　　　　　110　　　　　　　　　115 | | 392 |
| gtg tac tct cat cta ttt tcg tgg gca gct gaa gtg gcg cgt gaa gtc<br>Val Tyr Ser His Leu Phe Ser Trp Ala Ala Glu Val Ala Arg Glu Val<br>　　　120　　　　　　　　　125　　　　　　　　　130 | | 440 |
| gac gtg ccg agt gcc ctt ctt tgg att gaa ccg gct acg gtt ttc gat<br>Asp Val Pro Ser Ala Leu Leu Trp Ile Glu Pro Ala Thr Val Phe Asp<br>135　　　　　　　　　140　　　　　　　　　145 | | 488 |
| gtg tac tat ttt tac ttc aat ggg tat gcc gat gat atc gat gcg ggc<br>Val Tyr Tyr Phe Tyr Phe Asn Gly Tyr Ala Asp Asp Ile Asp Ala Gly<br>　　150　　　　　　　　　155　　　　　　　　　160 | | 536 |
| tca gat caa atc caa ctg ccc aat ctt ccg cag ctc tcc aag caa gat<br>Ser Asp Gln Ile Gln Leu Pro Asn Leu Pro Gln Leu Ser Lys Gln Asp<br>165　　　　　　　　　170　　　　　　　　　175　　　　　　　　　180 | | 584 |
| ctc ccc tct ttc cta ctc cct tcg agc ccc gcg aga ttc cga acc cta<br>Leu Pro Ser Phe Leu Leu Pro Ser Ser Pro Ala Arg Phe Arg Thr Leu<br>　　　　　　　185　　　　　　　　　190　　　　　　　　　195 | | 632 |
| atg aaa gaa aag ttc gac acg ctc gac aaa gaa ccg aaa gcg aag gtc<br>Met Lys Glu Lys Phe Asp Thr Leu Asp Lys Glu Pro Lys Ala Lys Val<br>　　　　　　　200　　　　　　　　　205　　　　　　　　　210 | | 680 |
| ttg ata aac acg ttc gac gca tta gaa acc gaa caa ctc aaa gcc atc<br>Leu Ile Asn Thr Phe Asp Ala Leu Glu Thr Glu Gln Leu Lys Ala Ile<br>　　　　　　　215　　　　　　　　　220　　　　　　　　　225 | | 728 |
| gac agg tat gaa cta ata tcc atc ggc cca tta atc cca tca tcg ata<br>Asp Arg Tyr Glu Leu Ile Ser Ile Gly Pro Leu Ile Pro Ser Ser Ile<br>　　230　　　　　　　　　235　　　　　　　　　240 | | 776 |
| ttc tca gat ggc aac gac ccc tca tca agc aac aaa tcc tac ggt gga<br>Phe Ser Asp Gly Asn Asp Pro Ser Ser Ser Asn Lys Ser Tyr Gly Gly<br>245　　　　　　　　　250　　　　　　　　　255　　　　　　　　　260 | | 824 |
| gac ctc ttc aga aaa gcc gat gaa act tac atg gac tgg cta aac tca<br>Asp Leu Phe Arg Lys Ala Asp Glu Thr Tyr Met Asp Trp Leu Asn Ser<br>　　　　　　　265　　　　　　　　　270　　　　　　　　　275 | | 872 |
| aaa ccc gaa tca tcg gtc gtt tac gtt tcg ttc ggg agc ctc ctg agg<br>Lys Pro Glu Ser Ser Val Val Tyr Val Ser Phe Gly Ser Leu Leu Arg<br>　　　　　　　280　　　　　　　　　285　　　　　　　　　290 | | 920 |
| ctc ccg aaa ccc caa atg gaa gaa ata gca ata ggg ctt tca gac acc<br>Leu Pro Lys Pro Gln Met Glu Glu Ile Ala Ile Gly Leu Ser Asp Thr<br>　　　　295　　　　　　　　　300　　　　　　　　　305 | | 968 |
| aaa tcg cca gtt ctc tgg gtg ata aga aga aac gaa gag ggc gac gaa<br>Lys Ser Pro Val Leu Trp Val Ile Arg Arg Asn Glu Glu Gly Asp Glu<br>310　　　　　　　　　315　　　　　　　　　320 | | 1016 |
| caa gag caa gca gaa gaa gaa gag aag ctg ctg agc ttc ttt gat cgt<br>Gln Glu Gln Ala Glu Glu Glu Lys Leu Leu Ser Phe Phe Asp Arg<br>325　　　　　　　　　330　　　　　　　　　335　　　　　　　　　340 | | 1064 |
| cac gga act gaa cga ctc ggg aaa atc gtg aca tgg tgc tca caa ttg<br>His Gly Thr Glu Arg Leu Gly Lys Ile Val Thr Trp Cys Ser Gln Leu<br>　　　　　　　345　　　　　　　　　350　　　　　　　　　355 | | 1112 |
| gat gtt ctg acg cat aag tcg gtg gga tgc ttc gtg acg cat tgc ggt<br>Asp Val Leu Thr His Lys Ser Val Gly Cys Phe Val Thr His Cys Gly<br>　　　　　　　360　　　　　　　　　365　　　　　　　　　370 | | 1160 |
| tgg aat tct gct atc gag agc ctg gct tgt ggt gtg ccc gtg gtg tgc<br>Trp Asn Ser Ala Ile Glu Ser Leu Ala Cys Gly Val Pro Val Val Cys<br>　　　　　　　375　　　　　　　　　380　　　　　　　　　385 | | 1208 |
| ttt cct caa tgg ttc gat caa ggg act aat gcg aag atg atc gaa gat<br>Phe Pro Gln Trp Phe Asp Gln Gly Thr Asn Ala Lys Met Ile Glu Asp<br>　　　　390　　　　　　　　　395　　　　　　　　　400 | | 1256 |
| gtg tgg agg agt ggt gtg aga gtc aga gtg aat gag gaa ggc ggc gtt<br>Val Trp Arg Ser Gly Val Arg Val Arg Val Asn Glu Glu Gly Gly Val<br>405　　　　　　　　　410　　　　　　　　　415　　　　　　　　　420 | | 1304 |

-continued

```
gtt gat agg cgt gag att aag agg tgc gtc tcg gag gtt ata aag agt     1352
Val Asp Arg Arg Glu Ile Lys Arg Cys Val Ser Glu Val Ile Lys Ser
            425                 430                 435 cga gag ttg aga gaa agc gca atg atg tgg aag ggt ttg gct aaa gaa     1400
Arg Glu Leu Arg Glu Ser Ala Met Met Trp Lys Gly Leu Ala Lys Glu
        440                 445                 450 gct atg gat gaa gaa cgt gga tca tca atg aac aat ctg aag aat ttt     1448
Ala Met Asp Glu Glu Arg Gly Ser Ser Met Asn Asn Leu Lys Asn Phe
            455                 460                 465 att act agg att att aat gaa aat gcc tca taagttgtac tatatatgtt       1498
Ile Thr Arg Ile Ile Asn Glu Asn Ala Ser
        470                 475 attattgttg ttatggacgt cgaattaagt attagttaaa tgatatgtat ttagaggaag   1558
gccaaaacgg gctacacccg gcaggccacg ggttggaaaa gcccgccatg atttaaaata   1618
tatattttaa aataaatatt ttctactatt aaactaaaaa aaaaaaaaaa aaa          1671
```

<210> SEQ ID NO 8
<211> LENGTH: 478
<212> TYPE: PRT
<213> ORGANISM: Torenia hybrira

<400> SEQUENCE: 8

```
Met Val Asn Lys Arg His Ile Leu Leu Ala Thr Phe Pro Ala Gln Gly
  1               5                  10                  15

His Ile Asn Pro Ser Leu Glu Phe Ala Lys Arg Leu Leu Asn Thr Gly
                 20                  25                  30

Tyr Val Asp Gln Val Thr Phe Phe Thr Ser Val Tyr Ala Leu Arg Arg
             35                  40                  45

Met Arg Phe Glu Thr Asp Pro Ser Ser Arg Ile Asp Phe Val Ala Xaa
         50                  55                  60

Xaa Asp Ser Tyr Asp Asp Gly Leu Lys Lys Gly Asp Gly Lys Asn
 65                  70                  75                  80

Tyr Met Ser Glu Met Arg Lys Arg Gly Thr Lys Ala Leu Lys Asp Thr
                 85                  90                  95

Leu Ile Lys Leu Asn Asp Ala Ala Met Gly Ser Glu Cys Tyr Asn Arg
            100                 105                 110

Val Ser Phe Val Val Tyr Ser His Leu Phe Ser Trp Ala Ala Glu Val
        115                 120                 125

Ala Arg Glu Val Asp Val Pro Ser Ala Leu Leu Trp Ile Glu Pro Ala
    130                 135                 140

Thr Val Phe Asp Val Tyr Tyr Phe Tyr Phe Asn Gly Tyr Ala Asp Asp
145                 150                 155                 160

Ile Asp Ala Gly Ser Asp Gln Ile Gln Leu Pro Asn Leu Pro Gln Leu
                165                 170                 175

Ser Lys Gln Asp Leu Pro Ser Phe Leu Leu Pro Ser Ser Pro Ala Arg
            180                 185                 190

Phe Arg Thr Leu Met Lys Glu Lys Phe Asp Thr Leu Asp Lys Glu Pro
        195                 200                 205

Lys Ala Lys Val Leu Ile Asn Thr Phe Asp Ala Leu Glu Thr Glu Gln
    210                 215                 220

Leu Lys Ala Ile Asp Arg Tyr Glu Leu Ile Ser Ile Gly Pro Leu Ile
225                 230                 235                 240

Pro Ser Ser Ile Phe Ser Asp Gly Asn Asp Pro Ser Ser Ser Asn Lys
                245                 250                 255
```

```
Ser Tyr Gly Gly Asp Leu Phe Arg Lys Ala Asp Glu Thr Tyr Met Asp
            260                 265                 270

Trp Leu Asn Ser Lys Pro Glu Ser Val Val Tyr Val Ser Phe Gly
        275                 280                 285

Ser Leu Leu Arg Leu Pro Lys Pro Gln Met Glu Glu Ile Ala Ile Gly
        290                 295                 300

Leu Ser Asp Thr Lys Ser Pro Val Leu Trp Val Ile Arg Arg Asn Glu
305                 310                 315                 320

Glu Gly Asp Glu Gln Glu Gln Ala Glu Glu Glu Lys Leu Leu Ser
                325                 330                 335

Phe Phe Asp Arg His Gly Thr Glu Arg Leu Gly Lys Ile Val Thr Trp
            340                 345                 350

Cys Ser Gln Leu Asp Val Leu Thr His Lys Ser Val Gly Cys Phe Val
            355                 360                 365

Thr His Cys Gly Trp Asn Ser Ala Ile Glu Ser Leu Ala Cys Gly Val
        370                 375                 380

Pro Val Val Cys Phe Pro Gln Trp Phe Asp Gln Gly Thr Asn Ala Lys
385                 390                 395                 400

Met Ile Glu Asp Val Trp Arg Ser Gly Val Arg Val Arg Val Asn Glu
                405                 410                 415

Glu Gly Gly Val Val Asp Arg Arg Glu Ile Lys Arg Cys Val Ser Glu
            420                 425                 430

Val Ile Lys Ser Arg Glu Leu Arg Glu Ser Ala Met Met Trp Lys Gly
            435                 440                 445

Leu Ala Lys Glu Ala Met Asp Glu Glu Arg Gly Ser Ser Met Asn Asn
        450                 455                 460

Leu Lys Asn Phe Ile Thr Arg Ile Ile Asn Glu Asn Ala Ser
465                 470                 475

<210> SEQ ID NO 9
<211> LENGTH: 1437
<212> TYPE: DNA
<213> ORGANISM: Perilla frutescens
<220> FEATURE:
<221> NAME/KEY: CDS
<222> LOCATION: (294)..(1298)

<400> SEQUENCE: 9
ttcaaaactc ataacgtgat tgagctaatg tgcacatctt cctcttcaaa gtctacagtg      60
tcatcctacc agcatcatca tgatcaatct ctttataatg aggagaatgg agtaacaagg     120
agtgggtttt gttactcagc ttcaacctac gtacgtacta ctactgactc aactctcaag     180
agaatgaata taatatataa tgggcgatag atctttgtag atatgtaggt gtagcctgca     240
ggtggttaat taatttccgg tgtgggaaaa taaataaata aataaatata gcg atg         296
                                                            Met
                                                             1 agc agc agc agc agc aga agg tgg aga gag aat gag ggg atg cga agg       344
Ser Ser Ser Ser Ser Arg Arg Trp Arg Glu Asn Glu Gly Met Arg Arg
            5                   10                  15 aca ttg ctg ggg ttg ggt ttg ggg cag ttg gtt tct ttc gat ttg gct       392
Thr Leu Leu Gly Leu Gly Leu Gly Gln Leu Val Ser Phe Asp Leu Ala
        20                  25                  30 atc atg acc ttt tct gct tct ttg gtt tca acc aca gtg gat gca cca       440
Ile Met Thr Phe Ser Ala Ser Leu Val Ser Thr Thr Val Asp Ala Pro
    35                  40                  45
```

```
ctt act atg tcg ttc act aca tac act gtt gtg gcc ctg ctc tat gga      488
Leu Thr Met Ser Phe Thr Thr Tyr Thr Val Val Ala Leu Leu Tyr Gly
 50              55                  60                  65 acc atc ttg ctt tac cgc cgc cac aaa ttc ttg gtt cca tgg tac tgg      536
Thr Ile Leu Leu Tyr Arg Arg His Lys Phe Leu Val Pro Trp Tyr Trp
             70                  75                  80 tat gct ctc ctg ggg ttc gtg gac gtc cac ggc aat tat ctt gtt aat      584
Tyr Ala Leu Leu Gly Phe Val Asp Val His Gly Asn Tyr Leu Val Asn
                 85                  90                  95 aaa gca ttc gag ttg aca tcg att acg agt gtg agc ata ctg gat tgt      632
Lys Ala Phe Glu Leu Thr Ser Ile Thr Ser Val Ser Ile Leu Asp Cys
        100                 105                 110 tgg aca atc gtg tgg tcc atc atc ttt aca tgg atg ttc cta ggc aca      680
Trp Thr Ile Val Trp Ser Ile Ile Phe Thr Trp Met Phe Leu Gly Thr
    115                 120                 125 aaa tac tct gta tac cag ttt gtc ggt gct gct att tgt gta gga ggc      728
Lys Tyr Ser Val Tyr Gln Phe Val Gly Ala Ala Ile Cys Val Gly Gly
130                 135                 140                 145 ctc ctc ctc gtg ctt ctt tcc gac tca ggg gtc act gct gct ggt tcg      776
Leu Leu Leu Val Leu Leu Ser Asp Ser Gly Val Thr Ala Ala Gly Ser
                150                 155                 160 aat cct ctt ttg ggt gat ttt ctt gtc ata aca ggc tct att ttg ttc      824
Asn Pro Leu Leu Gly Asp Phe Leu Val Ile Thr Gly Ser Ile Leu Phe
            165                 170                 175 aca ctc agc act gtt ggt cag gaa tac tgc gtg aag agg aaa gat cgt      872
Thr Leu Ser Thr Val Gly Gln Glu Tyr Cys Val Lys Arg Lys Asp Arg
        180                 185                 190 att gaa gta gta gca atg atc ggt gta ttt ggt atg ctc atc agt gca      920
Ile Glu Val Val Ala Met Ile Gly Val Phe Gly Met Leu Ile Ser Ala
    195                 200                 205 acc gag att act gtg ctg gag agg aat gcc ctc tca tca atg cag tgg      968
Thr Glu Ile Thr Val Leu Glu Arg Asn Ala Leu Ser Ser Met Gln Trp
210                 215                 220                 225 tct act gga ctt ttg gca gcc tat gtt gtt tat gca ctg tcc agc ttc     1016
Ser Thr Gly Leu Leu Ala Ala Tyr Val Val Tyr Ala Leu Ser Ser Phe
                230                 235                 240 ctc ttc tgc aca ctc acc cct ttt ctt ctc aag atg agt ggc gct gca     1064
Leu Phe Cys Thr Leu Thr Pro Phe Leu Leu Lys Met Ser Gly Ala Ala
            245                 250                 255 ttt ttc aat ctt tcc atg ctt aca tct gat atg tgg gct gtt gca att     1112
Phe Phe Asn Leu Ser Met Leu Thr Ser Asp Met Trp Ala Val Ala Ile
        260                 265                 270 agg aca ttc ata tac aac cag gag gtt gat tgg tta tac tat ttg gcc     1160
Arg Thr Phe Ile Tyr Asn Gln Glu Val Asp Trp Leu Tyr Tyr Leu Ala
    275                 280                 285 ttt tgt ctc gtt gtt gtt gga ata ttc ata tat aca aaa aca gag aag     1208
Phe Cys Leu Val Val Val Gly Ile Phe Ile Tyr Thr Lys Thr Glu Lys
290                 295                 300                 305 gat cct aac aat acg aga gcc ctt gag aat gga aac ttg gat cat gaa     1256
Asp Pro Asn Asn Thr Arg Ala Leu Glu Asn Gly Asn Leu Asp His Glu
                310                 315                 320 tat agt ctc ctt gag gat caa gat gac aca cca aga aaa cca              1298
Tyr Ser Leu Leu Glu Asp Gln Asp Asp Thr Pro Arg Lys Pro
            325                 330                 335 tagctagctt tgcccacaat cttttcatca acagttttaa ataattcgtg agggggagag   1358
agatcgagat actaattaat ggacgtctat tatatagttg gaggttttg ttttatttat    1418 ttatttgagt aaaaaaaaaa                                                1437
```

<210> SEQ ID NO 10
<211> LENGTH: 335
<212> TYPE: PRT
<213> ORGANISM: Perilla frutescens

<400> SEQUENCE: 10

| Met | Ser | Ser | Ser | Ser | Arg | Arg | Trp | Arg | Glu | Asn | Glu | Gly | Met | Arg |
| 1 | | | | 5 | | | | | 10 | | | | | 15 |

| Arg | Thr | Leu | Leu | Gly | Leu | Gly | Leu | Gly | Gln | Leu | Val | Ser | Phe | Asp | Leu |
| | | | 20 | | | | | 25 | | | | | 30 | | |

| Ala | Ile | Met | Thr | Phe | Ser | Ala | Ser | Leu | Val | Ser | Thr | Thr | Val | Asp | Ala |
| | | | 35 | | | | | 40 | | | | | 45 | | |

| Pro | Leu | Thr | Met | Ser | Phe | Thr | Thr | Tyr | Thr | Val | Val | Ala | Leu | Leu | Tyr |
| | 50 | | | | | 55 | | | | | 60 | | | | |

| Gly | Thr | Ile | Leu | Leu | Tyr | Arg | Arg | His | Lys | Phe | Leu | Val | Pro | Trp | Tyr |
| 65 | | | | | 70 | | | | | 75 | | | | | 80 |

| Trp | Tyr | Ala | Leu | Leu | Gly | Phe | Val | Asp | Val | His | Gly | Asn | Tyr | Leu | Val |
| | | | | 85 | | | | | 90 | | | | | 95 | |

| Asn | Lys | Ala | Phe | Glu | Leu | Thr | Ser | Ile | Thr | Ser | Val | Ser | Ile | Leu | Asp |
| | | | | 100 | | | | | 105 | | | | | 110 | |

| Cys | Trp | Thr | Ile | Val | Trp | Ser | Ile | Ile | Phe | Thr | Trp | Met | Phe | Leu | Gly |
| | | | 115 | | | | | 120 | | | | | 125 | | |

| Thr | Lys | Tyr | Ser | Val | Tyr | Gln | Phe | Val | Gly | Ala | Ala | Ile | Cys | Val | Gly |
| | | 130 | | | | | 135 | | | | | 140 | | | |

| Gly | Leu | Leu | Leu | Val | Leu | Leu | Ser | Asp | Ser | Gly | Val | Thr | Ala | Ala | Gly |
| 145 | | | | | 150 | | | | | 155 | | | | | 160 |

| Ser | Asn | Pro | Leu | Leu | Gly | Asp | Phe | Leu | Val | Ile | Thr | Gly | Ser | Ile | Leu |
| | | | | 165 | | | | | 170 | | | | | 175 | |

| Phe | Thr | Leu | Ser | Thr | Val | Gly | Gln | Glu | Tyr | Cys | Val | Lys | Arg | Lys | Asp |
| | | | 180 | | | | | 185 | | | | | 190 | | |

| Arg | Ile | Glu | Val | Val | Ala | Met | Ile | Gly | Val | Phe | Gly | Met | Leu | Ile | Ser |
| | | 195 | | | | | 200 | | | | | 205 | | | |

| Ala | Thr | Glu | Ile | Thr | Val | Leu | Glu | Arg | Asn | Ala | Leu | Ser | Ser | Met | Gln |
| | 210 | | | | | 215 | | | | | 220 | | | | |

| Trp | Ser | Thr | Gly | Leu | Leu | Ala | Ala | Tyr | Val | Val | Tyr | Ala | Leu | Ser | Ser |
| 225 | | | | | 230 | | | | | 235 | | | | | 240 |

| Phe | Leu | Phe | Cys | Thr | Leu | Thr | Pro | Phe | Leu | Leu | Lys | Met | Ser | Gly | Ala |
| | | | | 245 | | | | | 250 | | | | | 255 | |

| Ala | Phe | Phe | Asn | Leu | Ser | Met | Leu | Thr | Ser | Asp | Met | Trp | Ala | Val | Ala |
| | | | 260 | | | | | 265 | | | | | 270 | | |

| Ile | Arg | Thr | Phe | Ile | Tyr | Asn | Gln | Glu | Val | Asp | Trp | Leu | Tyr | Tyr | Leu |
| | | 275 | | | | | 280 | | | | | 285 | | | |

| Ala | Phe | Cys | Leu | Val | Val | Val | Gly | Ile | Phe | Ile | Tyr | Thr | Lys | Thr | Glu |
| | 290 | | | | | 295 | | | | | 300 | | | | |

| Lys | Asp | Pro | Asn | Asn | Thr | Arg | Ala | Leu | Glu | Asn | Gly | Asn | Leu | Asp | His |
| 305 | | | | | 310 | | | | | 315 | | | | | 320 |

| Glu | Tyr | Ser | Leu | Leu | Glu | Asp | Gln | Asp | Asp | Thr | Pro | Arg | Lys | Pro |
| | | | | 325 | | | | | 330 | | | | | 335 |

<210> SEQ ID NO 11
<211> LENGTH: 2105
<212> TYPE: DNA
<213> ORGANISM: Petunia hybrida
<220> FEATURE:
<221> NAME/KEY: CDS
<222> LOCATION: (341)..(1744)

<400> SEQUENCE: 11

```
agtgagcgca acgcaattaa tgtgagttag ctcactcatt aggcacccca ggctttacac    60
tttatgcttc cggctcgtat gttgtgtgga attgtgagcg ataacaatt tcacacagga   120 aacagctatg accatgatta cgccaagctc gaaattaacc ctcactaaag ggaacaaaag   180
ctggagctcc acgcggtggc ggccgctcta gaactagtgg atccccccggg ctgcaggaat   240 tccgttgctg tcgccacaat ttacaaacca agaaattaag catcccttc cccccttaa    300 aaaacataca agttttaat ttttcactaa gcaagaaaat atg gtg cag cct cat      355
                                             Met Val Gln Pro His
                                               1               5 gtc atc tta aca aca ttt cca gca caa ggc cat att aat cca gca ctt    403
Val Ile Leu Thr Thr Phe Pro Ala Gln Gly His Ile Asn Pro Ala Leu
             10                  15                  20 caa ttt gcc aag aat ctt gtc aag atg ggc ata gaa gtg aca ttt tct    451
Gln Phe Ala Lys Asn Leu Val Lys Met Gly Ile Glu Val Thr Phe Ser
         25                  30                  35 aca agc att tat gcc caa agc cgt atg gat gaa aaa tcc att ctt aat    499
Thr Ser Ile Tyr Ala Gln Ser Arg Met Asp Glu Lys Ser Ile Leu Asn
     40                  45                  50 gca cca aaa gga ttg aat ttc att cca ttt tcc gat ggc ttt gat gaa    547
Ala Pro Lys Gly Leu Asn Phe Ile Pro Phe Ser Asp Gly Phe Asp Glu
 55                  60                  65 ggt ttt gat cat tca aaa gac cct gta ttt tac atg tca caa ctt cgt    595
Gly Phe Asp His Ser Lys Asp Pro Val Phe Tyr Met Ser Gln Leu Arg
         70                  75                  80                 85 aaa tgt gga agt gaa act gtc aaa aaa ata att ctc act tgc tct gaa    643
Lys Cys Gly Ser Glu Thr Val Lys Lys Ile Ile Leu Thr Cys Ser Glu
                 90                  95                 100 aat gga cag cct ata act tgc cta ctt tac tcc att ttc ctt cct tgg    691
Asn Gly Gln Pro Ile Thr Cys Leu Leu Tyr Ser Ile Phe Leu Pro Trp
             105                 110                 115 gca gca gag gta gca cgt gaa gtt cac atc cct tct gct ctt ctt tgg    739
Ala Ala Glu Val Ala Arg Glu Val His Ile Pro Ser Ala Leu Leu Trp
         120                 125                 130 agt caa cca gca aca ata ttg gac ata tat tac ttc aac ttt cat gga    787
Ser Gln Pro Ala Thr Ile Leu Asp Ile Tyr Tyr Phe Asn Phe His Gly
     135                 140                 145 tat gaa aaa gct atg gct aat gaa tcc aat gat cca aat tgg tcc att    835
Tyr Glu Lys Ala Met Ala Asn Glu Ser Asn Asp Pro Asn Trp Ser Ile
150                 155                 160                 165 caa ctt ccc ggg ctt cca cta ctg gaa act cga gat ctt cct tca ttt    883
Gln Leu Pro Gly Leu Pro Leu Leu Glu Thr Arg Asp Leu Pro Ser Phe
             170                 175                 180 tta ctt cct tat ggt gca aaa ggg agt ctt cga gtt gca ctt cca cca    931
Leu Leu Pro Tyr Gly Ala Lys Gly Ser Leu Arg Val Ala Leu Pro Pro
         185                 190                 195 ttc aaa gaa ttg ata gac aca tta gat gct gaa acc act cct aag att    979
Phe Lys Glu Leu Ile Asp Thr Leu Asp Ala Glu Thr Thr Pro Lys Ile
     200                 205                 210 ctt gtg aat aca ttt gat gaa tta gag cct gag gca ctc aat gca att   1027
Leu Val Asn Thr Phe Asp Glu Leu Glu Pro Glu Ala Leu Asn Ala Ile
215                 220                 225 gaa ggt tat aag ttt tat gga att gga ccg ttg att cct tct gct ttc   1075
Glu Gly Tyr Lys Phe Tyr Gly Ile Gly Pro Leu Ile Pro Ser Ala Phe
         230                 235                 240                 245 ttg ggt gga aat gac cct tta gat gct tca ttt ggt ggt gat ctt ttt   1123
Leu Gly Gly Asn Asp Pro Leu Asp Ala Ser Phe Gly Gly Asp Leu Phe
             250                 255                 260
```

```
caa aat tca aat gac tat atg gaa tgg tta aac tca aag cca aat tca      1171
Gln Asn Ser Asn Asp Tyr Met Glu Trp Leu Asn Ser Lys Pro Asn Ser
            265                 270                 275 tca gtt gtt tat ata tct ttt ggg agt cta atg aat cca tct att agc      1219
Ser Val Val Tyr Ile Ser Phe Gly Ser Leu Met Asn Pro Ser Ile Ser
        280                 285                 290 caa atg gag gag ata tca aaa ggg ttg ata gac ata gga agg ccg ttt      1267
Gln Met Glu Glu Ile Ser Lys Gly Leu Ile Asp Ile Gly Arg Pro Phe
    295                 300                 305 tta tgg gtg ata aaa gaa aat gaa aaa ggc aaa gaa gaa gag aat aaa      1315
Leu Trp Val Ile Lys Glu Asn Glu Lys Gly Lys Glu Glu Glu Asn Lys
310                 315                 320                 325 aag ctt ggt tgt att gaa gaa ttg gaa aaa ata gga aaa ata gtt cca      1363
Lys Leu Gly Cys Ile Glu Glu Leu Glu Lys Ile Gly Lys Ile Val Pro
                330                 335                 340 tgg tgt tca caa ctt gaa gtt cta aaa cat cca tct tta gga tgt ttt      1411
Trp Cys Ser Gln Leu Glu Val Leu Lys His Pro Ser Leu Gly Cys Phe
            345                 350                 355 gtt tct cat tgt gga tgg aat tca gcc tta gag agt tta gct tgt gga      1459
Val Ser His Cys Gly Trp Asn Ser Ala Leu Glu Ser Leu Ala Cys Gly
        360                 365                 370 gtg cca gtt gtg gca ttt cct caa tgg aca gat caa atg aca aat gcc      1507
Val Pro Val Val Ala Phe Pro Gln Trp Thr Asp Gln Met Thr Asn Ala
    375                 380                 385 aaa caa gtt gaa gat gtg tgg aaa agt gga gta aga gtg aga ata aat      1555
Lys Gln Val Glu Asp Val Trp Lys Ser Gly Val Arg Val Arg Ile Asn
390                 395                 400                 405 gaa gat ggt gtt gtt gaa agt gag gaa atc aaa agg tgt att gaa ttg      1603
Glu Asp Gly Val Val Glu Ser Glu Glu Ile Lys Arg Cys Ile Glu Leu
                410                 415                 420 gta atg gat gga gga gag aaa ggg gaa gaa ttg aga aag aat gct aag      1651
Val Met Asp Gly Gly Glu Lys Gly Glu Glu Leu Arg Lys Asn Ala Lys
            425                 430                 435 aaa tgg aaa gaa ttg gct aga gaa gct gtg aag gaa ggt gga tct tca      1699
Lys Trp Lys Glu Leu Ala Arg Glu Ala Val Lys Glu Gly Gly Ser Ser
        440                 445                 450 cac aag aat tta aag gct ttt att gat gat gtt gcc aaa ggg ttt           1744
His Lys Asn Leu Lys Ala Phe Ile Asp Asp Val Ala Lys Gly Phe
    455                 460                 465 taatatttac aggcttttgc cgtgatatta cttcccctag ttggcgattc actctttgtg    1804
gacttgcttg acaaaaaact gagggaatgt gctaagacac gctaatgctt taagaagtca    1864
tttccaaggc ttgaagcctg cttttaaaac ttattagcca gtaatctata gggttctctt    1924
ctatttttct ctgtctctct ttttagcctt tttctttcca aggtttaaga atagcgtgaa    1984
catagcttag tacgtagtct tggtatctct atcttaccaa gtgcaagatt atgcttatgc    2044
tgtcctccta aatttcttaa taaaatgcaa gatgaaaaag tacaaaaaaa aaaaaaaaa    2104 a                                                                    2105

<210> SEQ ID NO 12
<211> LENGTH: 468
<212> TYPE: PRT
<213> ORGANISM: Petunia hybrida

<400> SEQUENCE: 12

Met Val Gln Pro His Val Ile Leu Thr Thr Phe Pro Ala Gln Gly His
 1               5                  10                  15

Ile Asn Pro Ala Leu Gln Phe Ala Lys Asn Leu Val Lys Met Gly Ile
            20                  25                  30
```

```
Glu Val Thr Phe Ser Thr Ser Ile Tyr Ala Gln Ser Arg Met Asp Glu
         35                  40                  45

Lys Ser Ile Leu Asn Ala Pro Lys Gly Leu Asn Phe Ile Pro Phe Ser
 50                  55                  60

Asp Gly Phe Asp Glu Gly Phe Asp His Ser Lys Asp Pro Val Phe Tyr
 65                  70                  75                  80

Met Ser Gln Leu Arg Lys Cys Gly Ser Glu Thr Val Lys Lys Ile Ile
             85                  90                  95

Leu Thr Cys Ser Glu Asn Gly Gln Pro Ile Thr Cys Leu Leu Tyr Ser
            100                 105                 110

Ile Phe Leu Pro Trp Ala Ala Glu Val Ala Arg Glu Val His Ile Pro
        115                 120                 125

Ser Ala Leu Leu Trp Ser Gln Pro Ala Thr Ile Leu Asp Ile Tyr Tyr
130                 135                 140

Phe Asn Phe His Gly Tyr Glu Lys Ala Met Ala Asn Glu Ser Asn Asp
145                 150                 155                 160

Pro Asn Trp Ser Ile Gln Leu Pro Gly Leu Pro Leu Glu Thr Arg
                165                 170                 175

Asp Leu Pro Ser Phe Leu Leu Pro Tyr Gly Ala Lys Gly Ser Leu Arg
            180                 185                 190

Val Ala Leu Pro Pro Phe Lys Glu Leu Ile Asp Thr Leu Asp Ala Glu
        195                 200                 205

Thr Thr Pro Lys Ile Leu Val Asn Thr Phe Asp Glu Leu Glu Pro Glu
    210                 215                 220

Ala Leu Asn Ala Ile Glu Gly Tyr Lys Phe Tyr Gly Ile Gly Pro Leu
225                 230                 235                 240

Ile Pro Ser Ala Phe Leu Gly Gly Asn Asp Pro Leu Asp Ala Ser Phe
            245                 250                 255

Gly Gly Asp Leu Phe Gln Asn Ser Asn Asp Tyr Met Glu Trp Leu Asn
        260                 265                 270

Ser Lys Pro Asn Ser Ser Val Val Tyr Ile Ser Phe Gly Ser Leu Met
    275                 280                 285

Asn Pro Ser Ile Ser Gln Met Glu Glu Ile Ser Lys Gly Leu Ile Asp
290                 295                 300

Ile Gly Arg Pro Phe Leu Trp Val Ile Lys Glu Asn Glu Lys Gly Lys
305                 310                 315                 320

Glu Glu Glu Asn Lys Lys Leu Gly Cys Ile Glu Glu Leu Glu Lys Ile
            325                 330                 335

Gly Lys Ile Val Pro Trp Cys Ser Gln Leu Glu Val Leu Lys His Pro
        340                 345                 350

Ser Leu Gly Cys Phe Val Ser His Cys Gly Trp Asn Ser Ala Leu Glu
    355                 360                 365

Ser Leu Ala Cys Gly Val Pro Val Val Ala Phe Pro Gln Trp Thr Asp
370                 375                 380

Gln Met Thr Asn Ala Lys Gln Val Glu Asp Val Trp Lys Ser Gly Val
385                 390                 395                 400

Arg Val Arg Ile Asn Glu Asp Gly Val Val Glu Ser Glu Glu Ile Lys
            405                 410                 415

Arg Cys Ile Glu Leu Val Met Asp Gly Gly Glu Lys Gly Glu Glu Leu
        420                 425                 430

Arg Lys Asn Ala Lys Lys Trp Lys Glu Leu Ala Arg Glu Ala Val Lys
    435                 440                 445
```

```
                                    -continued
Glu Gly Gly Ser Ser His Lys Asn Leu Lys Ala Phe Ile Asp Asp Val
    450                 455                 460

Ala Lys Gly Phe
465
```